United States Patent
Smith et al.

(10) Patent No.: US 12,384,993 B2
(45) Date of Patent: Aug. 12, 2025

(54) BIOREACTOR

(71) Applicant: The Trustees of Indiana University, Indianapolis, IN (US)

(72) Inventors: Lester Jeshua Smith, Maud, TX (US); Brian Paul McCarthy, Indianapolis, IN (US); Mark Robert Holland, McCordsville, IN (US); Paul Richard Territo, Fishers, IN (US)

(73) Assignee: The Trustees of Indiana University, Bloomington, IN (US)

( * ) Notice: Subject to any disclaimer, the term of this patent is extended or adjusted under 35 U.S.C. 154(b) by 582 days.

(21) Appl. No.: 17/396,816

(22) Filed: Aug. 9, 2021

(65) Prior Publication Data

US 2021/0371783 A1 Dec. 2, 2021

Related U.S. Application Data

(63) Continuation of application No. 16/261,526, filed on Jan. 29, 2019, now abandoned.

(60) Provisional application No. 62/623,921, filed on Jan. 30, 2018.

(51) Int. Cl.

| | |
|---|---|
| *C12M 3/00* | (2006.01) |
| *A01N 1/143* | (2025.01) |
| *C12M 1/00* | (2006.01) |
| *C12M 1/34* | (2006.01) |
| *B33Y 10/00* | (2015.01) |
| *B33Y 30/00* | (2015.01) |
| *C12N 5/00* | (2006.01) |

(52) U.S. Cl.
CPC ............. *C12M 21/08* (2013.01); *A01N 1/143* (2025.01); *C12M 23/38* (2013.01); *C12M 29/10* (2013.01); *C12M 41/36* (2013.01); *B33Y 10/00* (2014.12); *B33Y 30/00* (2014.12); *C12N 5/0062* (2013.01)

(58) Field of Classification Search
CPC ....................................... C12M 21/08
See application file for complete search history.

(56) References Cited

U.S. PATENT DOCUMENTS

| | | | |
|---|---|---|---|
| 8,158,427 B2 * | 4/2012 | Wilson ................... | C12M 23/24 435/297.5 |
| 8,507,266 B2 | 8/2013 | Welter et al. | |
| 9,399,755 B2 * | 7/2016 | Karerangabo ......... | C12M 25/06 |
| 2011/0136225 A1 | 6/2011 | Vunjak-Novakovic et al. | |
| 2012/0129257 A1 * | 5/2012 | Yu .......................... | C12M 23/46 435/395 |
| 2015/0064780 A1 * | 3/2015 | Hopkins ................ | C12M 29/10 435/325 |

OTHER PUBLICATIONS

Cartmell, Sarah H., et.. al., "Effects of Medium Perfusion Rate on Cell-Seeded Three-Dimensional Bone Constructi n Vitro*," Tissue Engineering, Vol. 9, No. 6, 1197-1203 (2003).

(Continued)

*Primary Examiner* — Jonathan M Hurst
(74) *Attorney, Agent, or Firm* — Taft Stettinius & Hollister LLP

(57) ABSTRACT

A bioreactor comprising a housing defining a perfusion chamber, the housing including at least one port, wherein the at least one port is coupled to the housing, and a sample holder positioned within the perfusion chamber. A bioreactor and spheroid-based biofabrication method for making perfusible tissue constructs and perfusing them.

21 Claims, 26 Drawing Sheets

(56) References Cited

OTHER PUBLICATIONS

Gaspar, Diana Alves, et. al., "The role of perfusion bioreactors in bone tissue engineering," Biomatter, vol. 2, No. 4, 1-9 (2012).
Sailon, Alexander M., et al., "A Novel Flow-Perfusion Bioreactor Supports 3D Dynamic Cell Culture," Journal of Biomedicine and Biotechnology, Article ID 873816, 1-7 (2009).
Territo, Paul R., et al., "Rapid Spectrophotometric Determination of Oxygen Consumption Using Hemoglobin, in Vitro: Light Scatter Correction and Expanded Dynamic Range," Analytical Biochemistry, vol. 286, 156-163 (2000).
,An der Helm, Marinke W, et. al., "Microfluidic organ—0n-chip technology for blood-brain barrier research," Tissue Barriers, vol. 4, No. 1, 1-13 (2016).
Sego, T. J., et. al., "Equalized Flow through Microchannels of Bioreactor SSuPer Modules," Poster presentation on Oct. 20-22, 2019.
Sego, T.J., et. al., "Equalized Flow through Microchannels of Bioreactor SSuPer Modules," Abstract publicly disclosed Oct. 20-22, 2019.
Sego, T.J., et. al., "Computational fluid dynamics analysis of bioprinted self-supporting perfused tissue models," Biotechnology Bioengineering, 1-18 (2019).
Smith, Lester J., et al., "Fabrica: A Bioreactor Platform for Printing, Perfusing, Observing, & Stimulating 3D Tissues," Scientific Reports, vol. 8, 1-10 (2018).

\* cited by examiner

BIOREACTOR

RELATED APPLICATIONS

The present disclosure is a continuation of U.S. Patent Application Ser. No. 16/261,526 filed on Jan. 29, 2018 and is related to and claims priority to U.S. Provisional Application No. 62/623,921, filed Jan. 30, 2018, entitled "BIOREACTOR," the entire disclosure of which is are hereby expressly incorporated by reference.

STATEMENT REGARDING FEDERALLY SPONSORED RESEARCH OR DEVELOPMENT

This invention was made with government support under OD023595 awarded by National Institutes of Health. The government has certain rights in the invention.

FIELD OF DISCLOSURE

The present disclosure relates generally to a bioreactor. In particular, the present disclosure relates to a bioreactor configured to permit tissue construct perfusion and mitigate risks associated with handling and transferring tissue constructs from printing vessels to incubation and/or perfusion vessels.

BACKGROUND OF DISCLOSURE

Bioprinting or biofabrication is used to produce tissue constructs from cells. These tissue constructs are then either investigated as models of tissue development or tissue pathology or prepared as replacements of damaged or destroyed tissues. However, following bioprinting, tissue constructs must often be contained in a system whereby tissues can culture or incubate for days to months and in some cases these tissues need to be perfused with nutrients. In current modes of tissue bioprinting, the tissues must be transferred from the printing vessel to an incubation and/or perfusion vessel, requiring the user to manually handle the tissue construct, which can be dropped or inadvertently contaminated. Thus, it would be beneficial to have a device that mitigates the risks associated with handling and transferring the tissue construct from the printing vessel to the culture/perfusion vessel.

SUMMARY OF THE DISCLOSURE

In one embodiment of the present disclosure, a modular bioreactor is disclosed comprising a housing defining a perfusion chamber, the housing including at least one port, wherein the at least one port is coupled to the housing, a sample holder positioned within the perfusion chamber, detachable modules for applying biological agents to tissues contained within the perfusion chamber at biologically relevant rates in the process of maturing biofabricated tissues, and detachable modules for aseptically ascertaining conditions within the perfusion chamber.

In one embodiment of the bioreactor, the at least one port is an analyzing port configured to receive at least one of a sensor and an imaging device.

In another embodiment of the bioreactor, the at least one of the sensor and the imaging device is one of an optical device and an infrared device.

In a further embodiment of the bioreactor, the at least one port includes a first port and a second port, the first port comprising an inlet port into the housing and the second port comprising an outlet port from the housing.

In another embodiment of the bioreactor, the first port and the second port are integrally formed as a single one-piece structure with the housing.

In a further embodiment of the bioreactor, the bioreactor is part of a system comprising a pump and tubing, wherein a first section of the tubing couples the inlet port to the pump and a second section of the tubing couples to outlet port to the pump.

In another embodiment of the bioreactor, the at least one port further includes a third port, the third port including an analyzing port.

In a further embodiment of the bioreactor, the analyzing port is positioned between the inlet port and the outlet port.

In another embodiment of the bioreactor, the bioreactor further comprises a cover configured to couple with the housing to close off the perfusion chamber from atmosphere.

In another embodiment of the present disclosure, a bioreactor is disclosed comprising a housing configured to define a perfusion chamber; and a sample holder positioned within the perfusion chamber; wherein the housing includes at least one observation port.

In one embodiment of the bioreactor, the housing further includes a cover configured to couple with the housing to close of the perfusion chamber from the atmosphere, and the at least one observation port is an analyzing portion within the cover.

In another embodiment of the bioreactor, the at least one observation port is an analyzing port positioned within a wall of the housing.

In yet another embodiment of the present disclosure, a bioreactor is disclosed comprising a housing configured to define a perfusion chamber, and a sample holder positioned within the perfusion chamber, the sample holder including a base and a platen configured to be positioned in abutment with the base, wherein the platen includes at least one handling extension.

In one embodiment of the bioreactor, the base includes at least one securing extension configured to hold the platen in abutment with the base.

In another embodiment of the bioreactor, the at least one securing extension includes two separate securing extensions.

In a further embodiment of the bioreactor, the sample holder further includes at least one perfusion opening extending through the base and the platen.

In another embodiment of the bioreactor, the platen further includes a skirt extending from a bottom surface of the platen.

In a further embodiment of the bioreactor, the at least one handling extension includes two handling extension, each of the two handling extensions being positioned to either side of the at least one perfusion opening.

In yet another embodiment of the present disclosure, a method for preparing a tissue construct is disclosed comprising the steps of filling a bioreactor with a fluid, the bioreactor including a housing defining a perfusion chamber, and a sample holder positioned within the perfusion chamber, wherein the housing includes an inlet port and an outlet port, the inlet port and the outlet port being integrally formed as a single one-piece structure with the housing, placing the tissue construct onto the sample holder, and at least one of coupling the inlet port and the outlet port of the bioreactor to a perfusion pump, placing the bioreactor in an incubator, and manipulating the tissue construct within the bioreactor.

In one embodiment of the method, the method further includes observing the tissue construct through at least one observation port within the housing.

In another embodiment of the method, the method further includes transferring the bioreactor to a desired area.

In still another embodiment of the present disclosure, a method for preparing a tissue construct is disclosed comprising the steps of filling a bioreactor with a fluid, the bioreactor including a housing defining a perfusion chamber, and a sample holder positioned within the perfusion chamber, wherein the housing includes at least one observation port, placing the tissue construct onto the sample holder, and observing the tissue constructions through the at least one observation port.

In one embodiment of the method, the housing includes a cover and the at least one observation port is an analyzing portion of the cover.

In another embodiment of the method, the at least one observation port is a port positioned along a wall of the housing.

In a further embodiment of the method, the step of observing the tissue construct can occur simultaneously with the step of printing the tissue construct.

In yet another embodiment of the present disclosure, a bioreactor is disclosed comprising a housing configured to define a perfusion chamber, and a sample holder positioned within the perfusion chamber, the sample holder including a base and a platen configured to be positioned in abutment with the base, wherein the plate and the base include at least one perfusion opening configured to align with a channel within a tissue construct such that a fluid may be perfused through the base, the platen, and the tissue construct via a single channel.

In one embodiment of the bioreactor, the platen includes a plurality of perfusion openings, and each of a majority of the plurality of perfusion openings is configured to align with one of a plurality of channels within the tissue construct.

In yet another embodiment of the present disclosure, a bioreactor is disclosed comprising a housing configured to define a perfusion chamber, and a sample holder positioned within the perfusion chamber, the sample holder including a base and a platen configured to be positioned in abutment with the base, wherein at least one of the base and the platen includes at least one handling extension, wherein the housing further includes a cover configured to couple with the housing to regulate interaction between the perfusion chamber and the atmosphere, and at least one observation port configured to be an analyzing portion within the cover designed with acoustic properties which facilitate transmission and reception of a plurality of ultrasound signals configured for image formation and ultrasound-based fluid flow measurements to provide an aseptic management of the transmission and reception.

In one embodiment of the bioreactor, the base includes at least one securing extension configured to hold the platen in abutment with the base. In a variation, the at least one securing extension includes two separate securing extensions.

In another embodiment of the bioreactor, the sample holder further includes at least one perfusion opening extending through the base and the platen.

In yet another embodiment of the bioreactor, the platen further includes a skirt extending from a bottom surface of the platen. In a variation, the at least one handling extension includes two handling extension, each of the two handling extensions being positioned to adjacent a side of the at least one perfusion opening.

In still another embodiment of the present disclosure, the plurality of ultrasound signals includes biological and material properties.

In yet another embodiment of the present disclosure, a method for preparing a biologically active tissue construct made from cells and extracellular matrix is disclosed. The method comprises partially or fully filling a bioreactor with a biocompatible fluid, the bioreactor including a housing defining a perfusion chamber, and a sample holder positioned within the perfusion chamber, wherein the housing includes an inlet port and an outlet port, the inlet port and the outlet port being integrally formed as a single one-piece structure with the housing; placing the tissue construct into or onto a module associated with the sample holder; and at least one of: coupling the inlet port and the outlet port of the bioreactor to a perfusion pump, placing the bioreactor in an incubator, and manipulating the tissue construct within the bioreactor to apply at least one of nutritious perfusion and stimuli.

In one embodiment of the method, the method further comprises observing the tissue construct through at least one observation port within the housing. In a variation, the method further comprises transferring the bioreactor to a desired area.

In another embodiment of the method, the method further comprises including in the model, a base and a platen configured to be positioned in abutment with the base. In a variation, the method further comprises including in the housing, a cover and an analyzing portion of the cover.

In yet another embodiment of the method, the method further comprises including the at least one observation port being positioned along a wall of the housing.

In still another embodiment of the method, the method further comprises simultaneously performing observing the tissue construct and printing the tissue construct.

In still yet another embodiment of the method, the method further comprises generating the tissue construct such that the tissue construct is self-supporting and having one or more perfusion channels. In a variation, the method further comprises creating the one or more perfusion channels of the tissue construct using corresponding one or more needles of the platen.

In yet another embodiment of the present disclosure, a perfusible tissue construct capable of supporting the stress of its own weight when unsupported by any other structure or medium other than its own bulk or air is disclosed comprising a body removably attached to a platen configured to be positioned in abutment with a base of a sample holder disposed within a perfusion chamber, which contains a biocompatible fluid sufficient to maintain tissue viability, such that the tissue construct remains in alignment with a plurality of perfusion channels disposed in the tissue construct independent of an intervening non-tissue material penetrating through the tissue construct, wherein the platen and the base include at least one perfusion opening configured to align with at least one of the plurality of perfusion channels such that the fluid is perfused through the base, the platen, and the tissue construct.

In one embodiment of the perfusible tissue construct, at least one of the base and the platen includes a plurality of perfusion openings, each of a majority of the plurality of perfusion openings configured to align with at least one of the plurality of channels disposed in the tissue construct.

In another embodiment of the perfusible tissue construct, the sample holder includes a construct support configured to removably attach the body of the tissue to the platen. In a variation, the construct support includes an adhesive interface.

In yet another embodiment of the perfusible tissue construct, the tissue construct is capable of supporting its own weight without the support of any intervening mechanical support.

In yet another embodiment of the present disclosure, a bioreactor is provided that includes a platen containing a tissue construct is temporarily coupled to a base. The base is temporarily or removably coupled to a sample holder within a perfusion chamber. The bioreactor further includes a sample holder positioned within the perfusion chamber. The sample holder includes the base and a platen configured to be positioned in abutment with the base, wherein the platen and the base include at least one perfusion opening configured to align with a channel within the tissue construct such that a fluid can be perfused through the base, the platen, and the tissue construct via a single channel.

In yet another embodiment of the present disclosure, a method for biofabricating scaffold-free tissues is provided wherein a final biofabricated tissue is capable of supporting its own weight without the support of any intervening mechanical support. In one example, the biofabricated tissue can be perfused or otherwise supplied with nutrients during and following maturation.

In yet another embodiment of the present disclosure, a bioreactor is provided that includes a tissue adhered to a platen having a plurality of microchannels aligned with microchannels in the tissue.

In yet another embodiment of the present disclosure, a method for biofabricating tissues is provided. The method includes positioning a platen-sleeve subassembly having a platen and a sleeve into a cast mold; placing cellular spheroids into the platen-sleeve subassembly, the platen-sleeve subassembly being temporarily or removably coupled to the cast mold; contacting the spheroids with a floor of the platen to be adhered to or otherwise secured to the floor; allowing a passage of nutrients and media using an interface between the platen and walls of the platen (e.g., sleeve); fusing the spheroids with the platen to one another; removing the platen-sleeve assembly from the cast mold after a predetermined fusion period; placing the platen-sleeve assembly onto a perfusion module and placing the perfusion module in a perfusion chamber of a bioreactor; creating a negative volume when the cast mold is removed to generate channels in the resulting biofabricated tissue which are intrinsically aligned with perfusion openings in the platen such that a fluid can be perfused through the platen and the tissue construct; and generating a self-supporting tissue which is adhered to the platen having perfusion channels aligned with perfusion channels in the tissue construct without using intervening non-tissue materials penetrating through the tissue construct.

In yet another embodiment of the present disclosure, a device to fill space within a perfusion chamber, thereby reducing a volume needed to fill the perfusion chamber with medium (e.g., a space saver). In one example, bioreactor and mold components are designed to remain sterile during a handling possess such that the device can be aseptically handled with forceps. In another example, a perfusion bioreactor is designed to fit within the confines of standard cell culture equipment such as plate holders and automated biomaterial handling systems.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The foregoing aspects and many of the intended advantages of this disclosure will become more readily appreciated as the same becomes better understood by reference to the following detailed description when taken in conjunction with the accompanying drawing.

Figure 1:
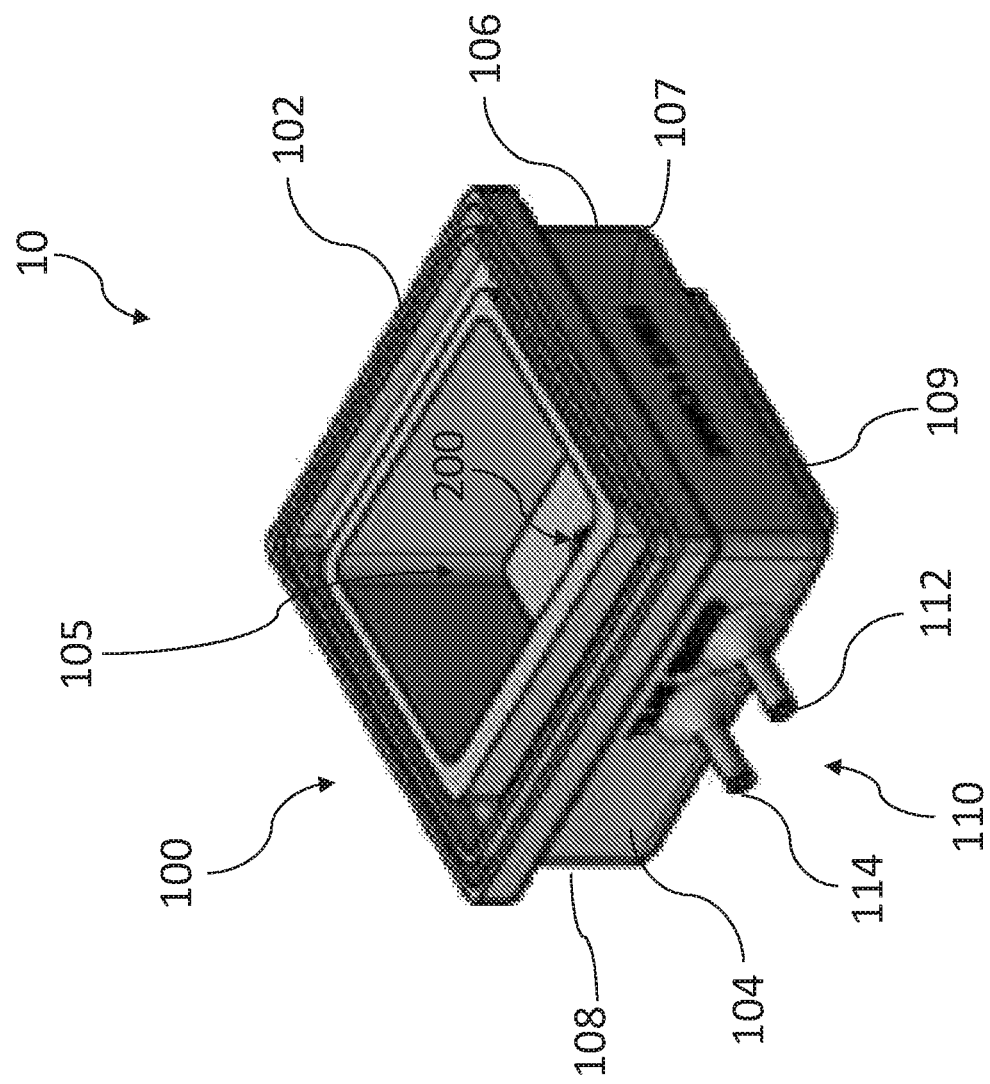
FIG. 1 shows a perspective view of an embodiment of a bioreactor of the present disclosure including an inlet port and an outlet port.

Although the drawing represents an embodiment of various features and components according to the present disclosure, the drawing is not necessarily to scale and certain features may be exaggerated in order to better illustrate and explain the present disclosure. The exemplification set out herein illustrates embodiments of the disclosure, and such exemplifications are not to be construed as limiting the scope of the disclosure in any manner.

DETAILED DESCRIPTION

For the purposes of promoting an understanding of the principals of the disclosure, reference will now be made to the embodiment illustrated in the drawing, which is described below. The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the disclosure is thereby intended. The disclosure includes any alterations and further modifications in the illustrative devices and described methods and further applications of the principles of the disclosure which would normally occur to one skilled in the art to which the disclosure relates.

Figure 2:
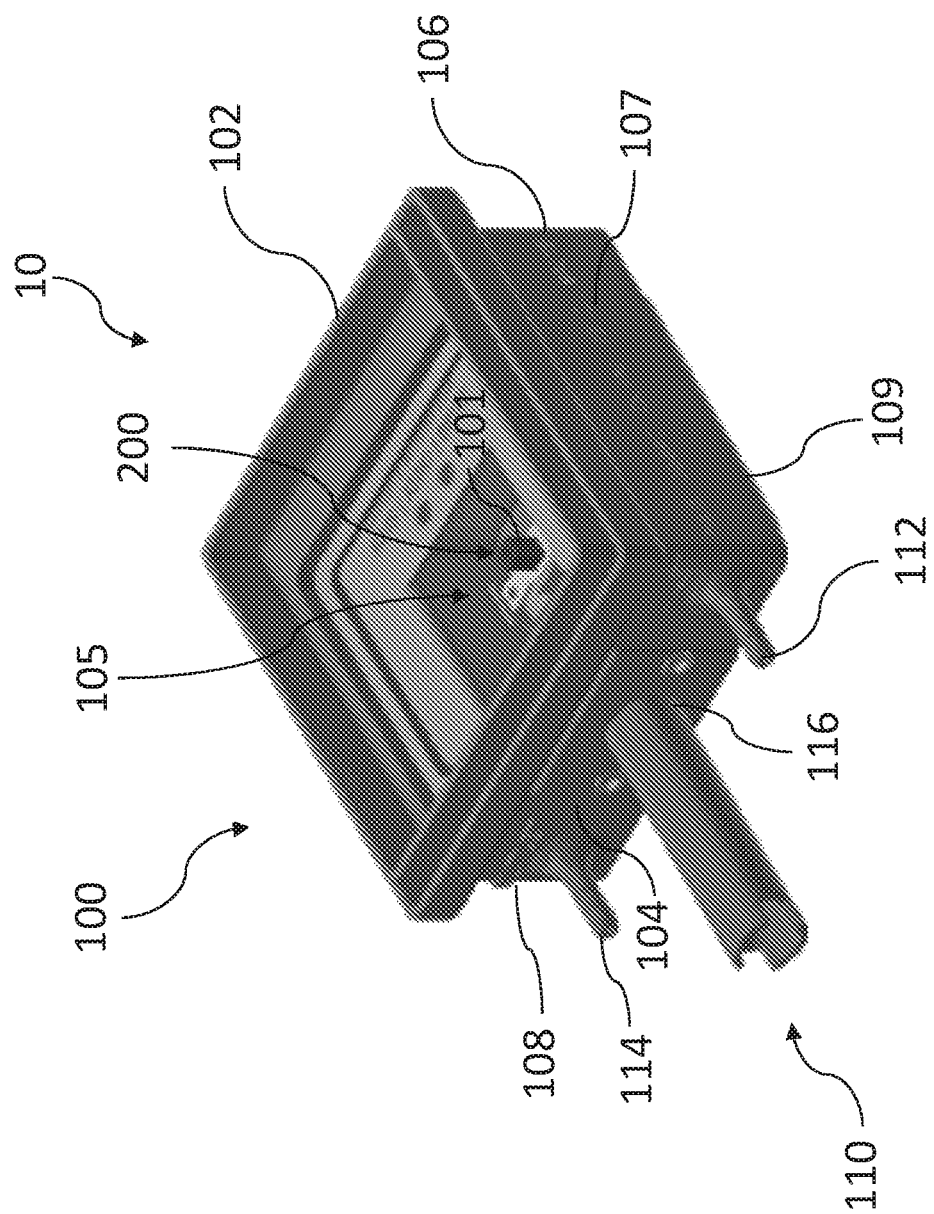
FIG. 2 shows a perspective view of another embodiment of a bioreactor of the present disclosure including an inlet port, an outlet port, and an observing/analyzing port.
Figure 3:
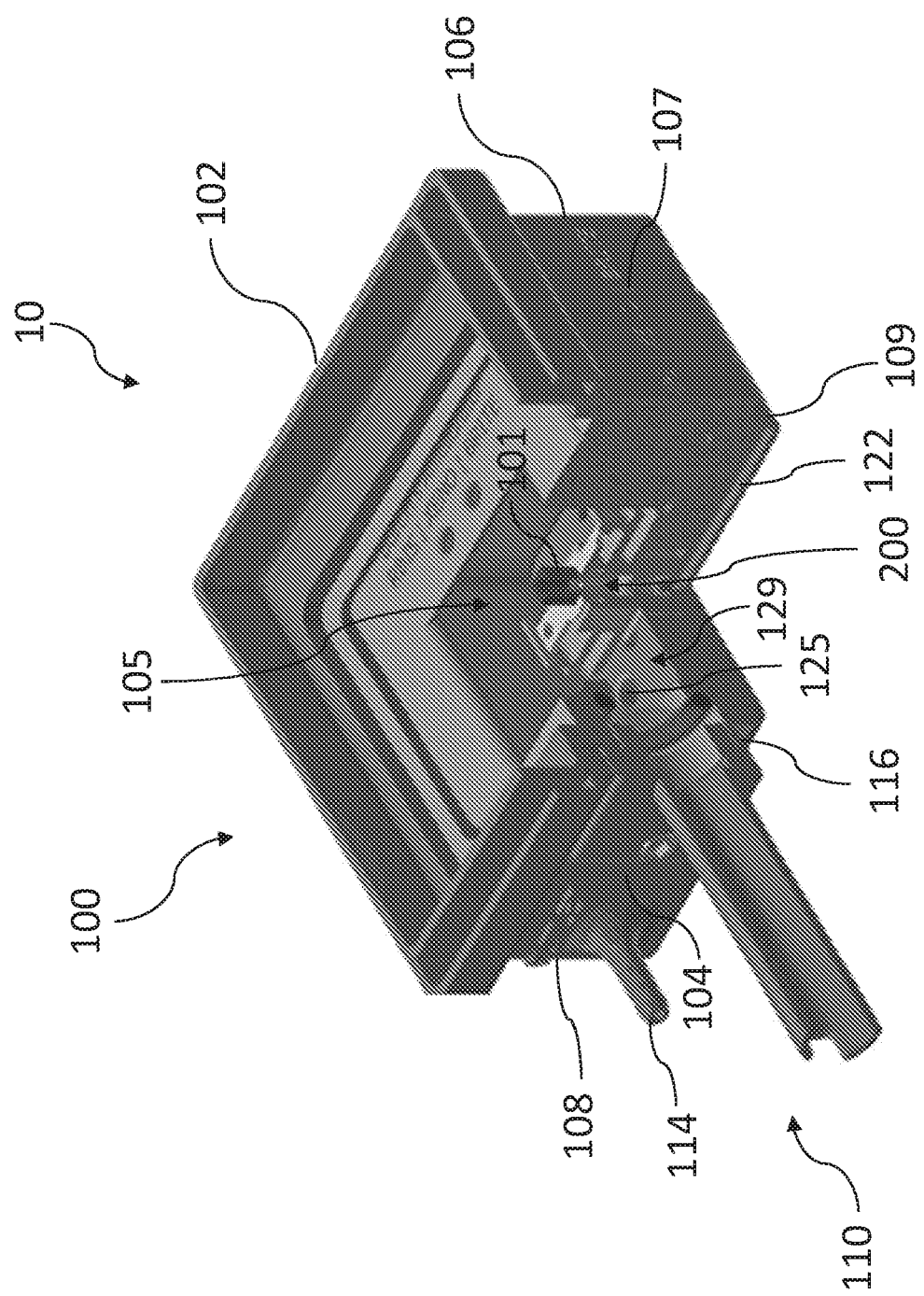
FIG. 3 shows a sectioned perspective view of the bioreactor of FIG. 2.

A bioreactor is disclosed for three-dimensional bioprinting, incubating, manipulating, perfusing, and/or observing/analyzing tissue constructs. Referring to FIGS. 1-3, a bioreactor 10 of the present disclosure comprises a housing 100 defining a perfusion chamber 105 and a sample holder 200 positioned within perfusion chamber 105. In general, bioreactor 10 is configured to house a tissue construct 101 within perfusion chamber 105 such that tissue construct 101 can be analyzed, manipulated, transferred and/or incubated without removing construct 101 from bioreactor 10. In various embodiments, bioreactor 10 is 3D-printed with material that is biocompatible and/or can be sterilized to further reduce the risk of contamination of perfusion chamber 105 and tissue construct 101.

With reference to FIGS. 1-5, housing 100 of bioreactor 10 comprises a lower housing 102 that defines a perfusion chamber 105 within which tissue constructs 101 can be placed on sample holder 200 and incubated, perfused, transferred, manipulated, and/or observed/analyzed. Lower housing 102 includes a front wall 104, a back wall 106, a first side wall 107, a second side wall 108, and a bottom 109. In various embodiments, lower housing 102 includes at least one port 110. The at least one port 110 may, in various embodiments, be integrally formed as a single one-piece structure with lower housing 102. The at least one port 110 may be formed on any of walls 104, 106, 107, or 108. The at least one port 110 may include an inlet port 112, an outlet port 114, and/or an observing/analyzing port 116. For example, in one embodiment, the at least one port 110 may include only observing/analyzing port 116, while in another embodiment, the at least one port may include only inlet port 112 and outlet port 114. In yet another embodiment, the at least one port may include all of ports 112, 114, and 116.

When housing 100 includes only inlet port 112 and outlet port 114, ports 112 and 114 may be spaced apart such that each port is closer to the adjacent walls, or ports 112 and 114 may be relatively close to one another and spaced apart from the adjacent walls. In various embodiments, inlet port 112 and outlet port 114 may be on separate walls of lower housing 102. For example, inlet port 112 may be positioned along front wall 104, while outlet port is positioned alongside wall 107 or 108 or back wall 106.

Figure 4:
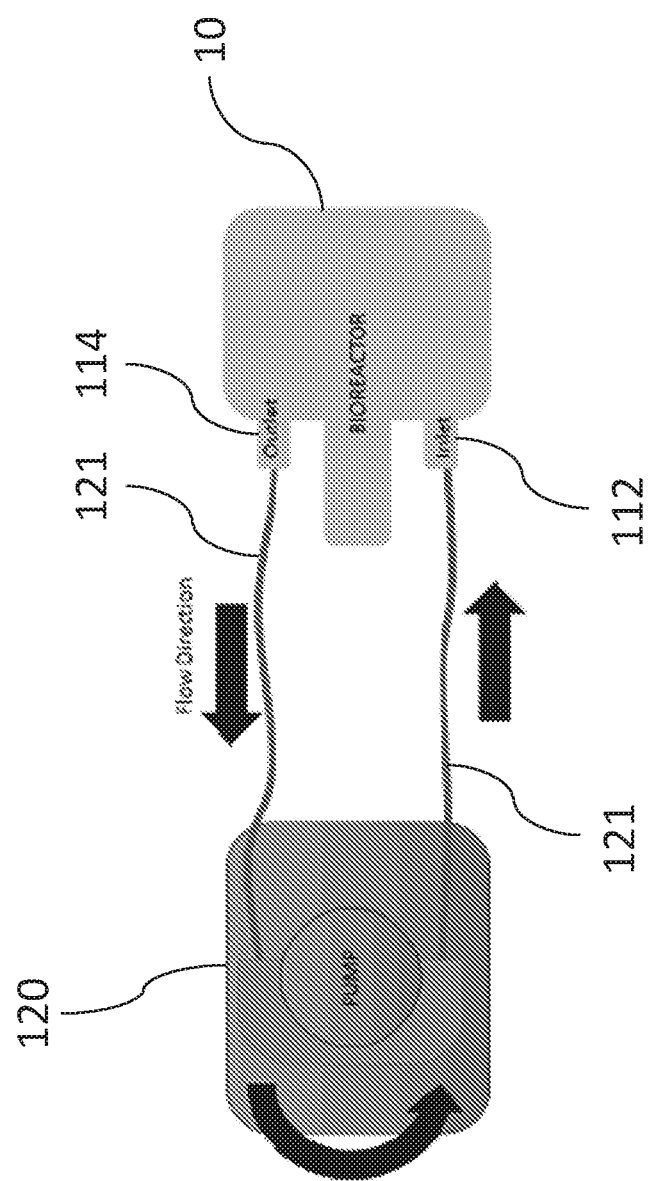
FIG. 4 shows a diagram of an embodiment of a system of the present disclosure including a bioreactor and a pump.
Figure 5:
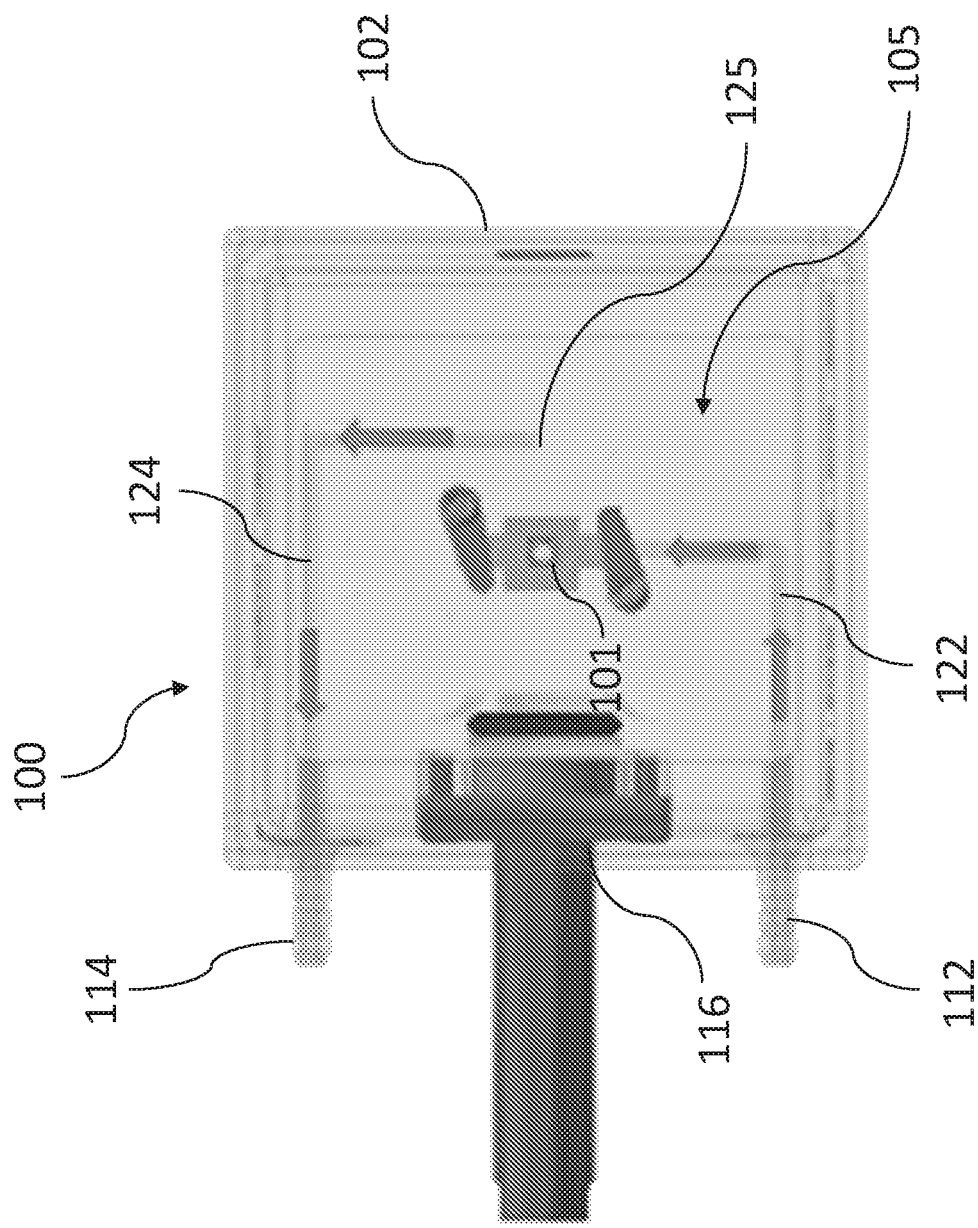
FIG. 5 shows a semi-transparent top view of the bioreactor of FIG. 2.

Referring now to FIGS. 3-5, in various embodiments, inlet port 112 and outlet port 114 are generally configured to couple to a pump 120 via tubing 121. By coupling lower housing 102 to pump 120, tissue construct 101 can be perfused with various fluids. The fluids generally circulated through lower housing 102 and perfusion chamber 105, and therefore perfused through tissue construct 101, include water, drug solutions, imaging solutions, nutrient enriched culture media such as blood of various source (i.e., animal or human), cell culture medium (CCM), or Dulbecco's modified eagle medium (DMEM), for example, or other similar fluids. In various embodiments, bioreactor 10 may be positioned within an incubator (not shown) and coupled to a pump 120 with connection tubes 121 coupling ports 112 and 114 of bioreactor 10 to pump 120. In addition, pump 120 may also be positioned within an incubator (not shown). In various embodiments, pump 120 may be a peristaltic pump or other similar pumps.

In order for the fluid to perfuse tissue construct 101, lower housing 102 includes an inlet flow channel 122 and an outlet flow channel 124 for directing the flow of the fluid through tissue construct 101. With reference to FIGS. 3 and 5, inlet flow channel 122 begins at inlet port 112 and extends thru bottom 109 of lower housing 102 until it is below sample holder 200 and tissue construct 101. This positioning allows the fluid to be directed through tissue construct 101 from the bottom of construct 101 to the top of construct 101 and then flow out into perfusion chamber 105. In various embodiments, inlet flow channel 122 may extend inward from inlet port 112 and make a 90 degree turn towards sample holder 200 and the bottom of construct 101.

Still referring to FIGS. 3 and 5, outlet flow channel 124 includes an inlet 125 provided along an upper surface 129 of bottom 109 of lower housing 102 and extends from inlet 125 to outlet port 114 such that fluid can be received from within perfusion chamber 105 and directed out of perfusion chamber 105 through outlet port 114. In various embodiments, inlet 125 is positioned proximate to sample holder 200 such that outlet flow channel 124 extends towards side 107 or 108 of housing 102 and then toward outlet port 114. The width of inlet flow channel 122 and outlet flow channel 124 may be varied during manufacturing depending on the desired flow velocity or volumetric flow rate required or other various characteristics.

Figure 6:
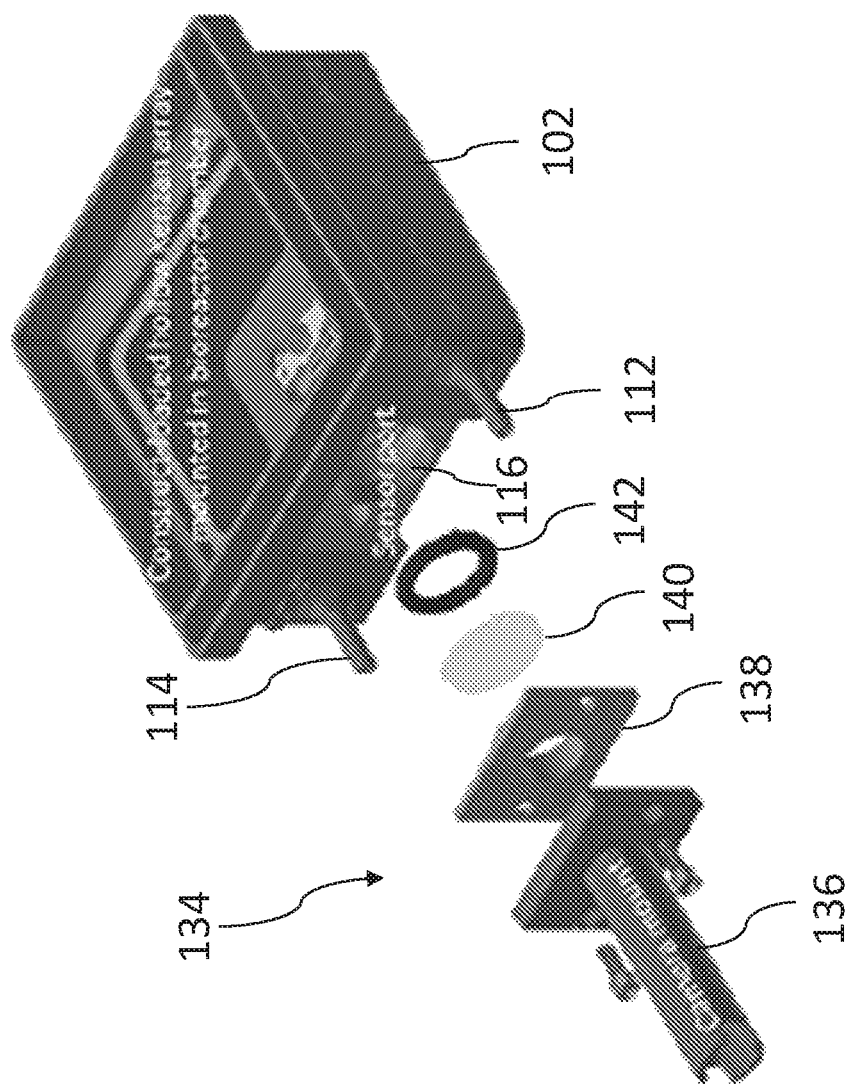
FIG. 6 shows an exploded view of a mount for a sensor or an imaging device coupled to an observing/analyzing port of the bioreactor of FIG. 2.

With reference now to FIGS. 2, 3, and 6, observation/analyzing port 116 allows a user to observe or analyze tissue construct 101 during and/or after placing tissue construct 101 within perfusion chamber 105. Observation/analyzing port 116 may support various sensors or imaging devices. Exemplary sensors or imaging devices may include a camera, an IR device, an ultrasound Doppler probe, or other similar sensors or imaging devices. In general, the sensor or imaging device is coupled to observation/analyzing port 116 of lower housing 102 via a mounting apparatus 134. Mounting apparatus 134 generally includes a device support 136, a coupling mount 138 for coupling device support 136 to lower housing 102, a lens 140, and a gasket 142. In various embodiments, gasket 142 is positioned between lens 140 and lower housing 102, and lens 140 is positioned between coupling mount 138 and gasket 142.

Figure 7:
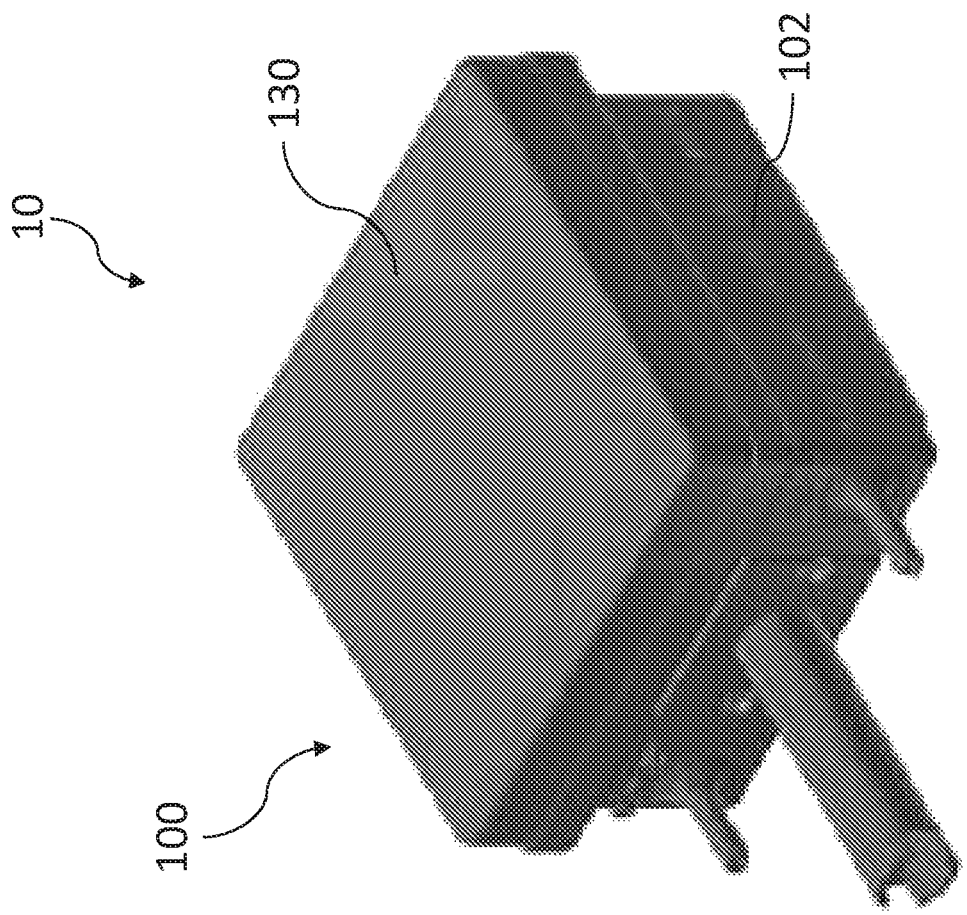
FIG. 7 shows the bioreactor of FIG. 2 with an embodiment of a cover of the present disclosure.
Figure 8:
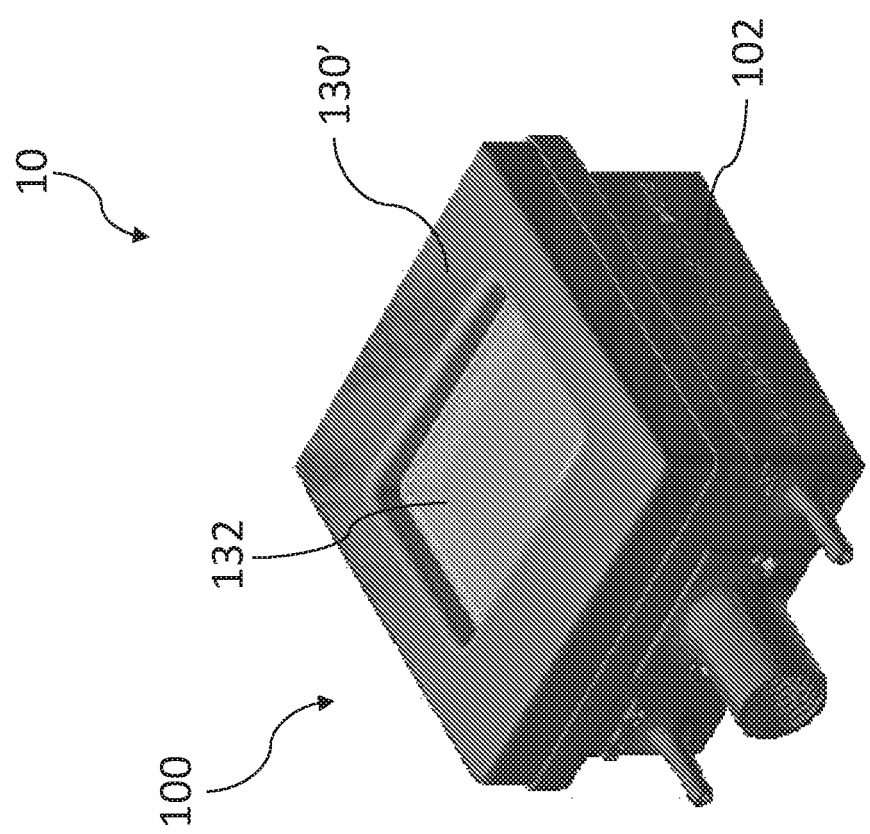
FIG. 8 shows the bioreactor of FIG. 2 with another embodiment of a cover of the present disclosure including an analyzing portion.
Figure 9:
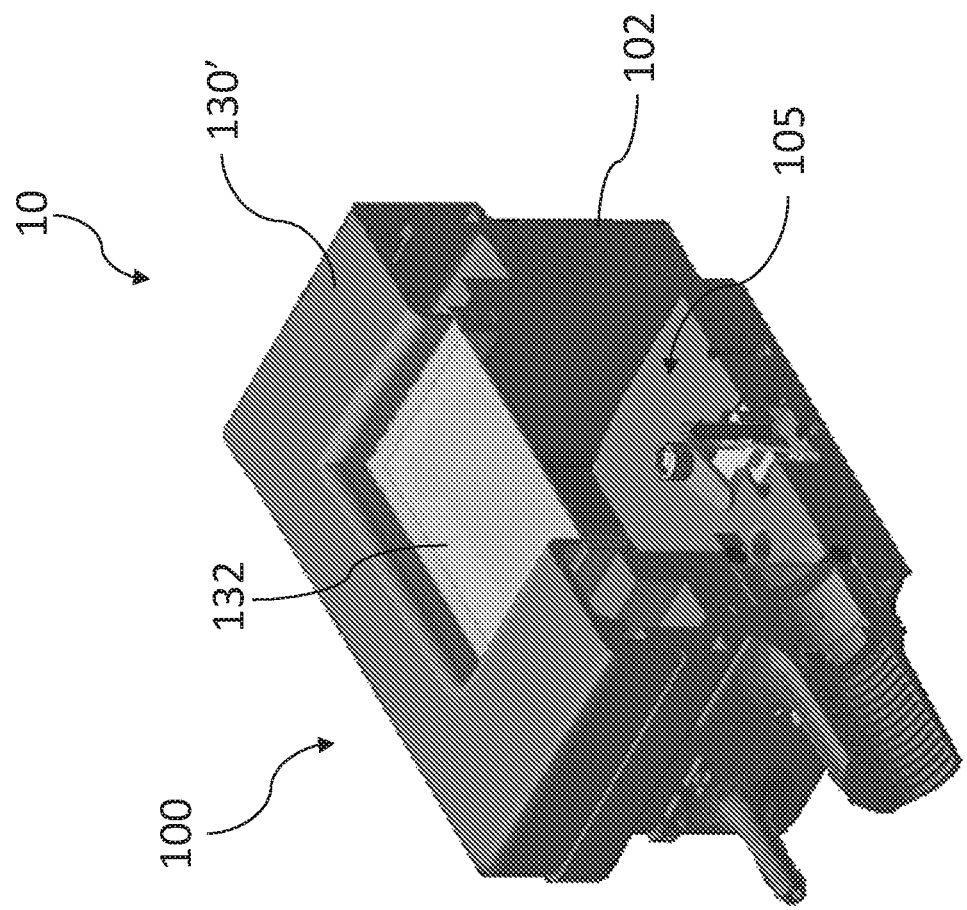
FIG. 9 shows a sectioned view of the bioreactor and the cover of FIG. 8.
Figure 10:
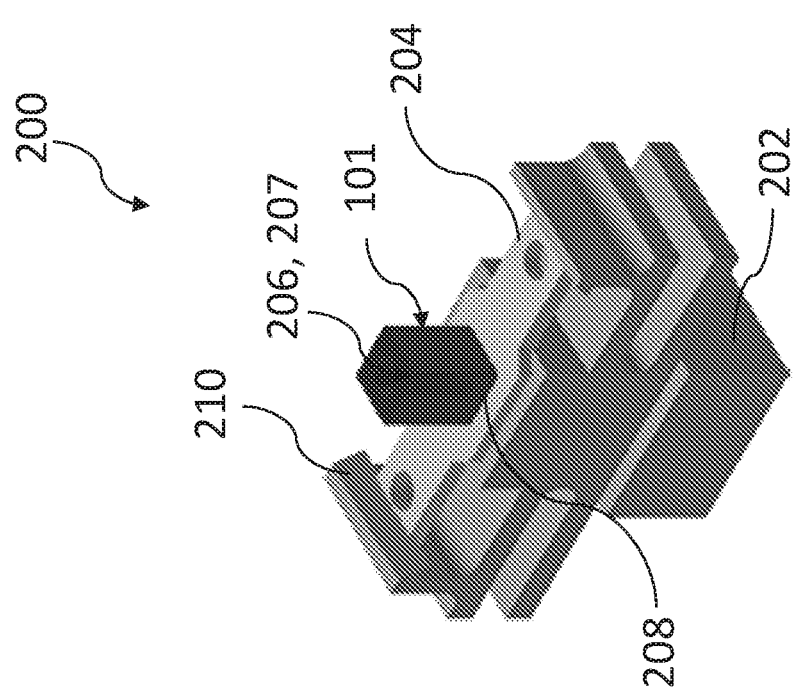
FIG. 10 shows a perspective view of an embodiment of a sample holder of the present disclosure having a base and a platen.
Figure 11:
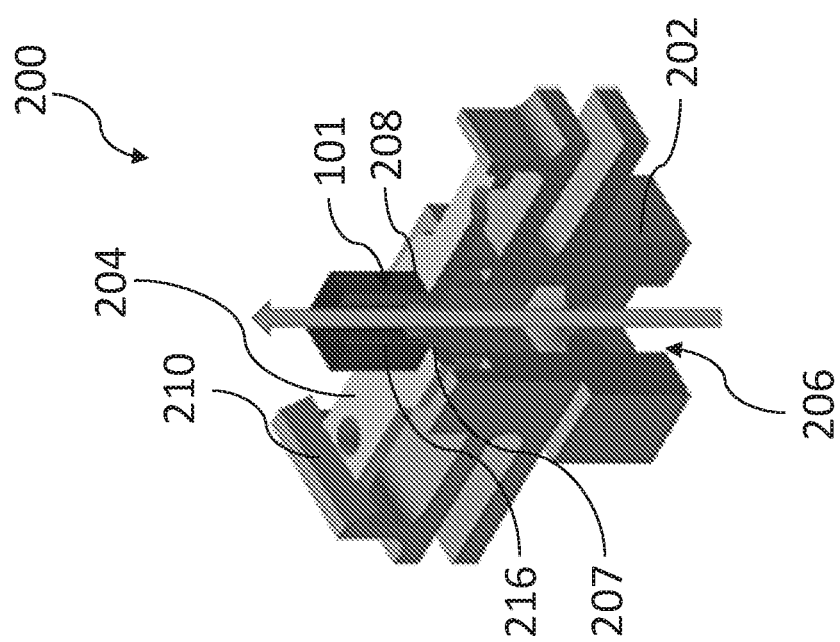
FIG. 11 shows a sectioned view of the sample holder of FIG. 10.
Figure 12:
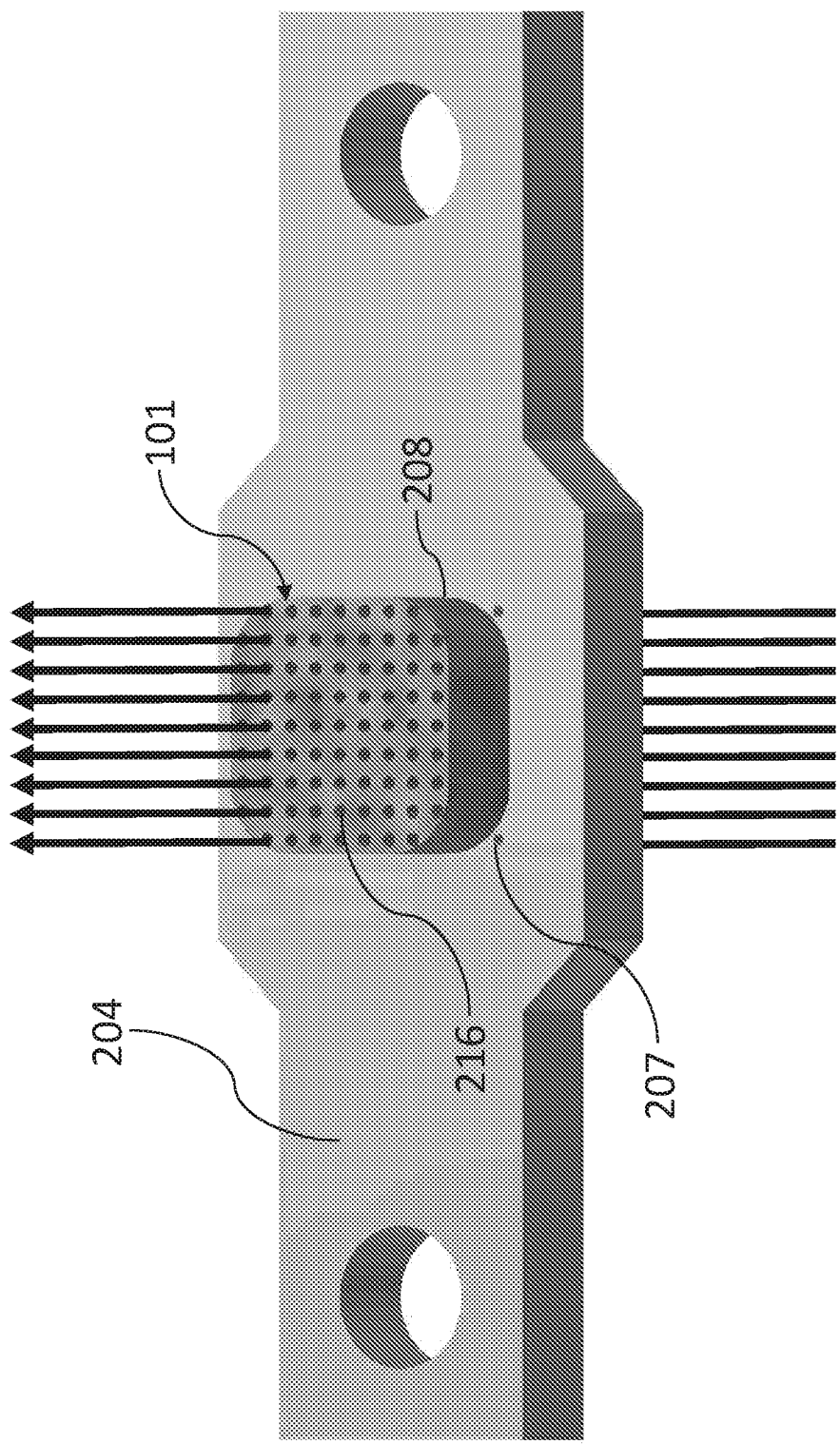
FIG. 12 shows a perspective view of the platen of the sample holder of FIG. 10.
Figure 13:
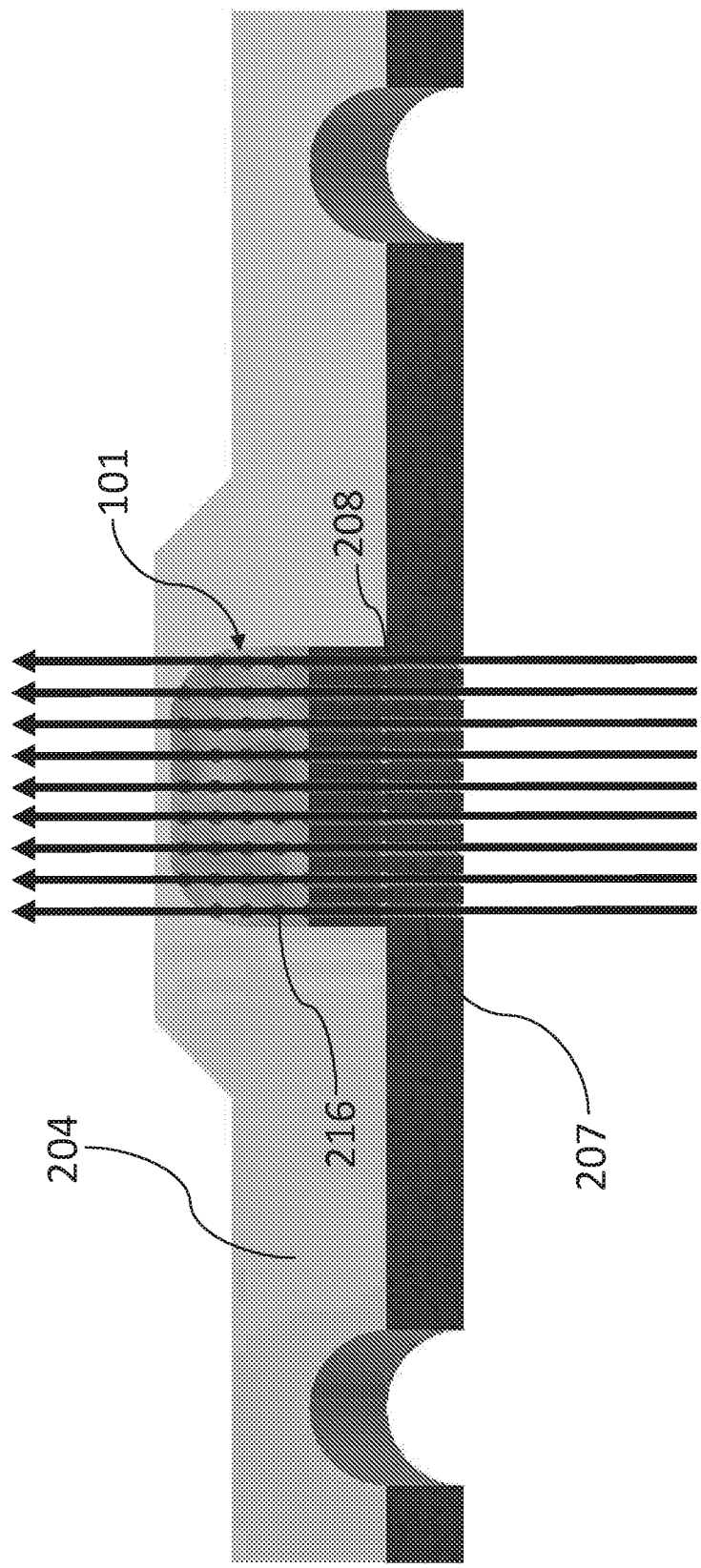
FIG. 13 shows a cross-sectional view of the platen of FIG. 12.
Figure 14:
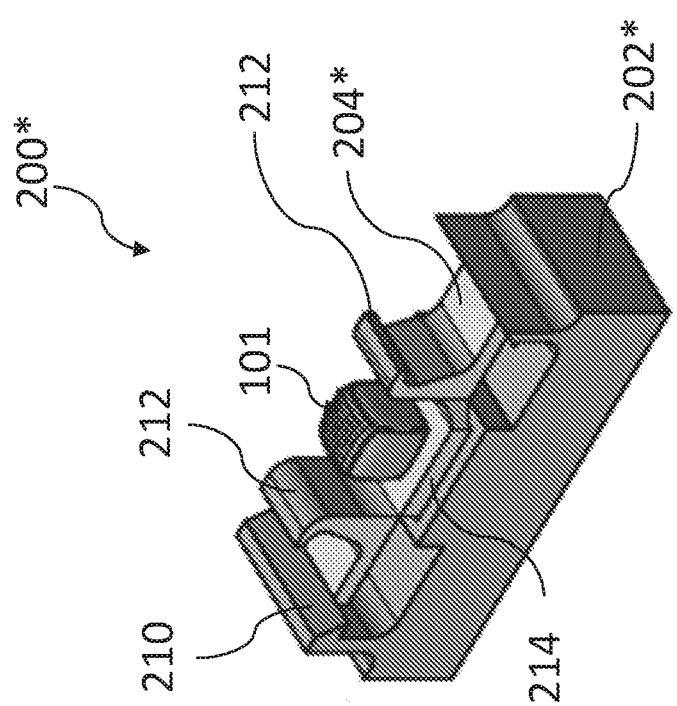
FIG. 14 shows a perspective view of another embodiment of a sample holder of the present disclosure.
Figure 15:
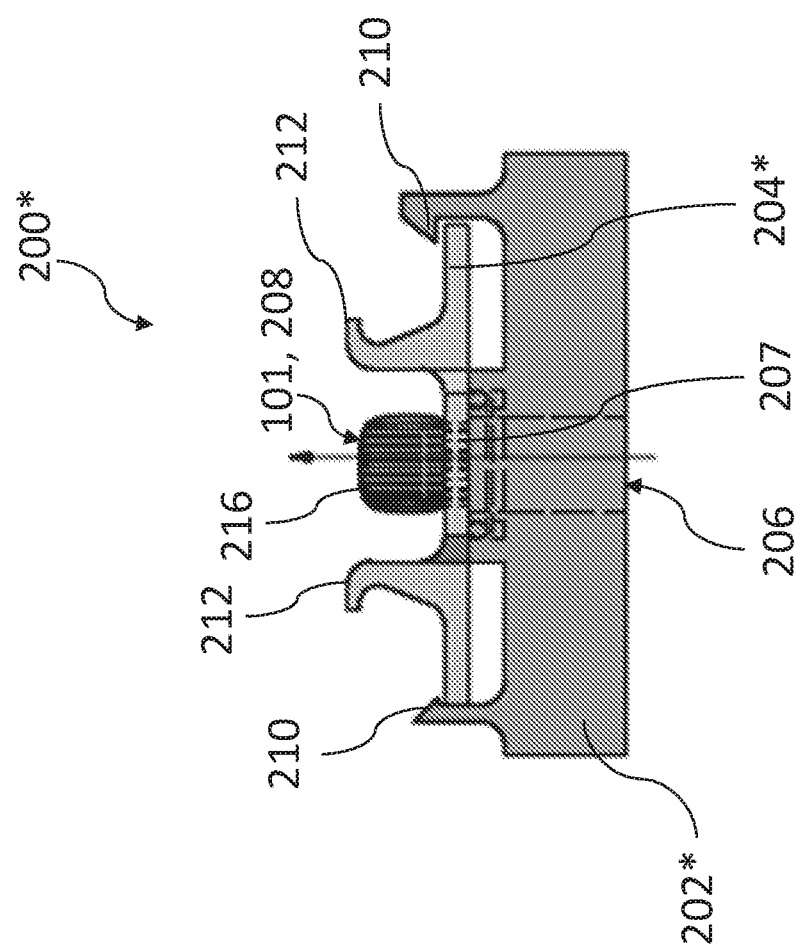
FIG. 15 shows a front semi-transparent view of the sample holder of FIG. 14.
Figure 16:
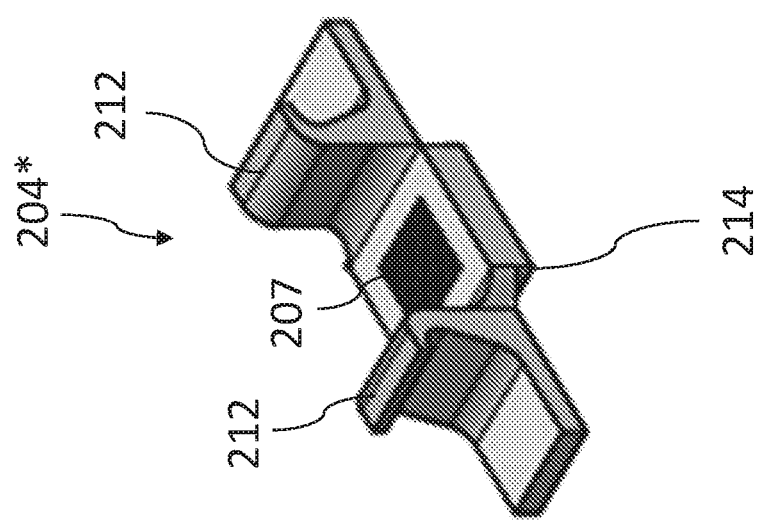
FIG. 16 shows a top perspective view of a platen of the sample holder of FIG. 14, the platen including handling extensions.
Figure 17:
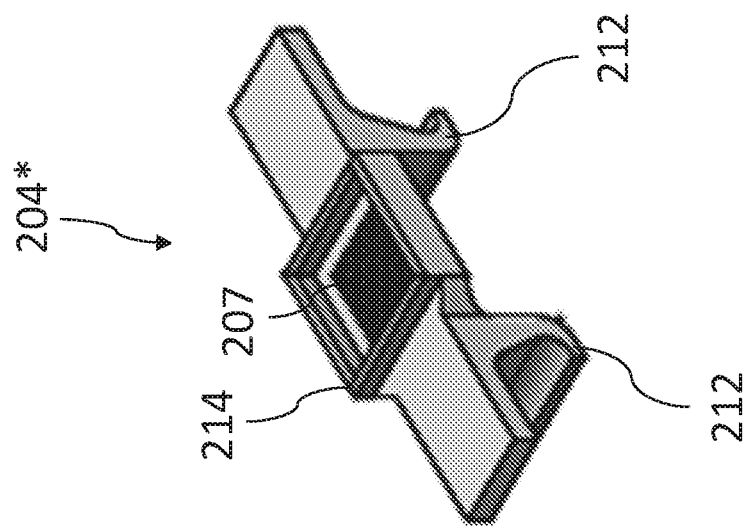
FIG. 17 shows a bottom perspective view of the platen of FIG. 16.
Figure 18:
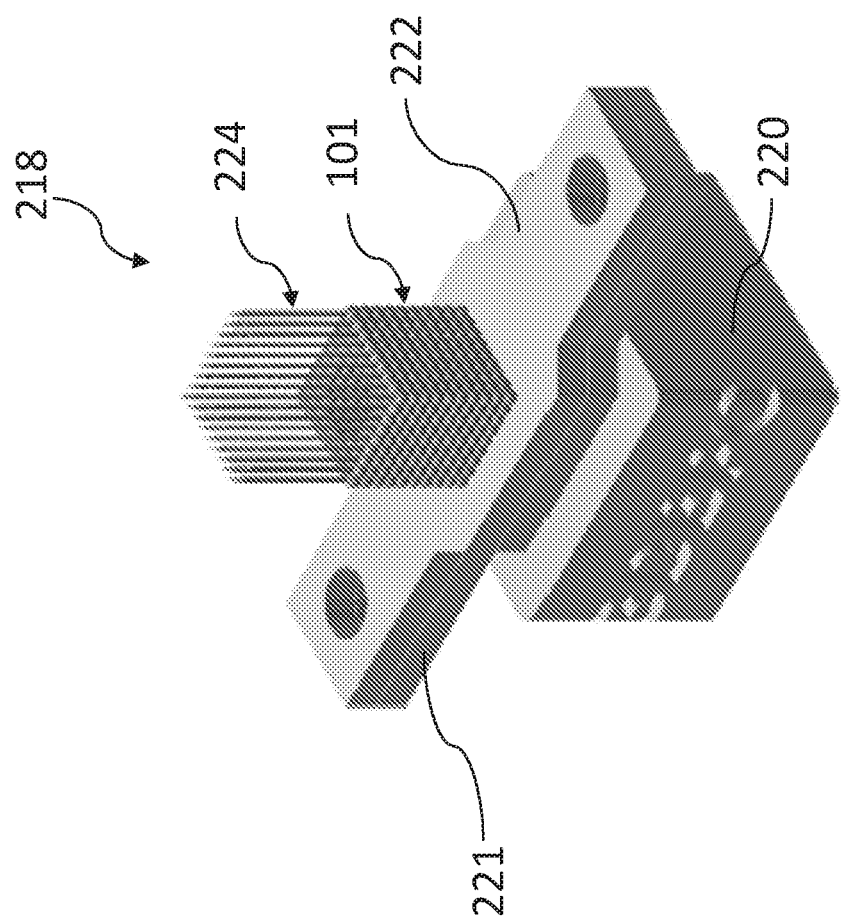
FIG. 18 shows a perspective view of an embodiment of a printing sample holder of the present disclosure.
Figure 19:
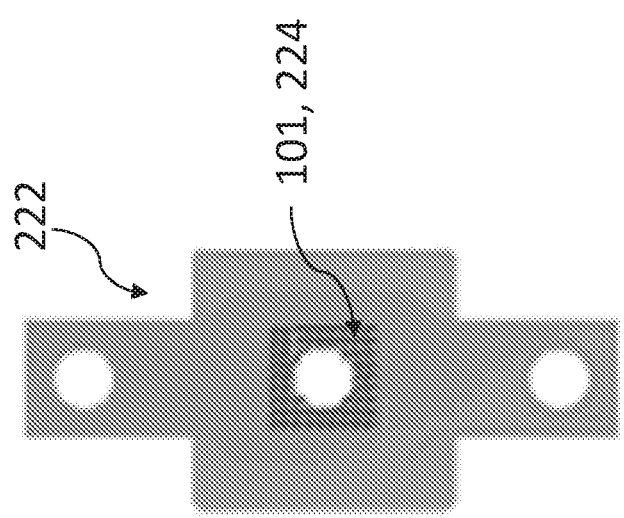
FIG. 19 shows a top view of the printing sample holder of FIG. 18.
Figure 20:
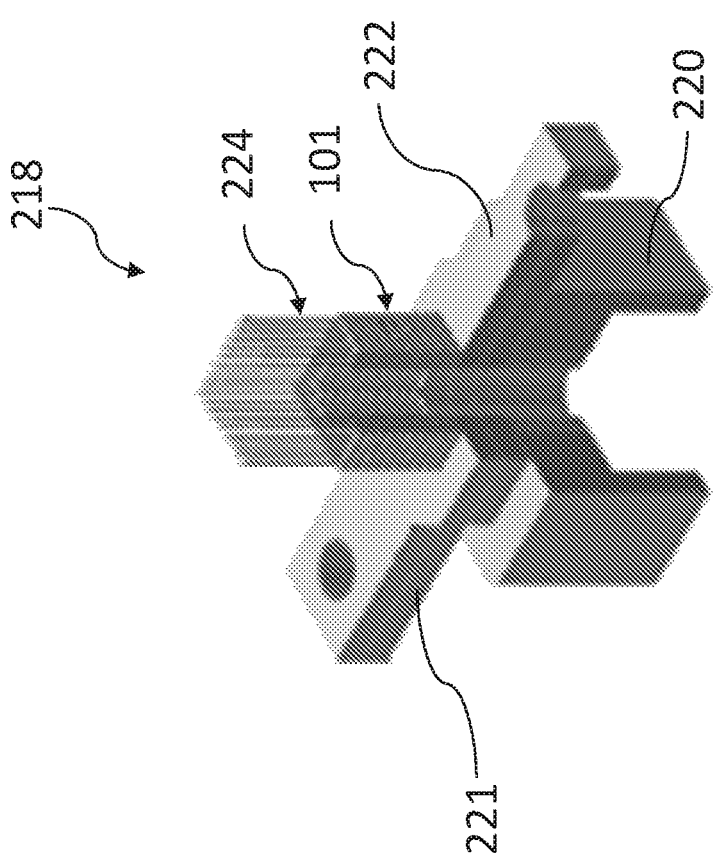
FIG. 20 shows a sectioned view of the printing sample holder of FIG. 18.
Figure 21:
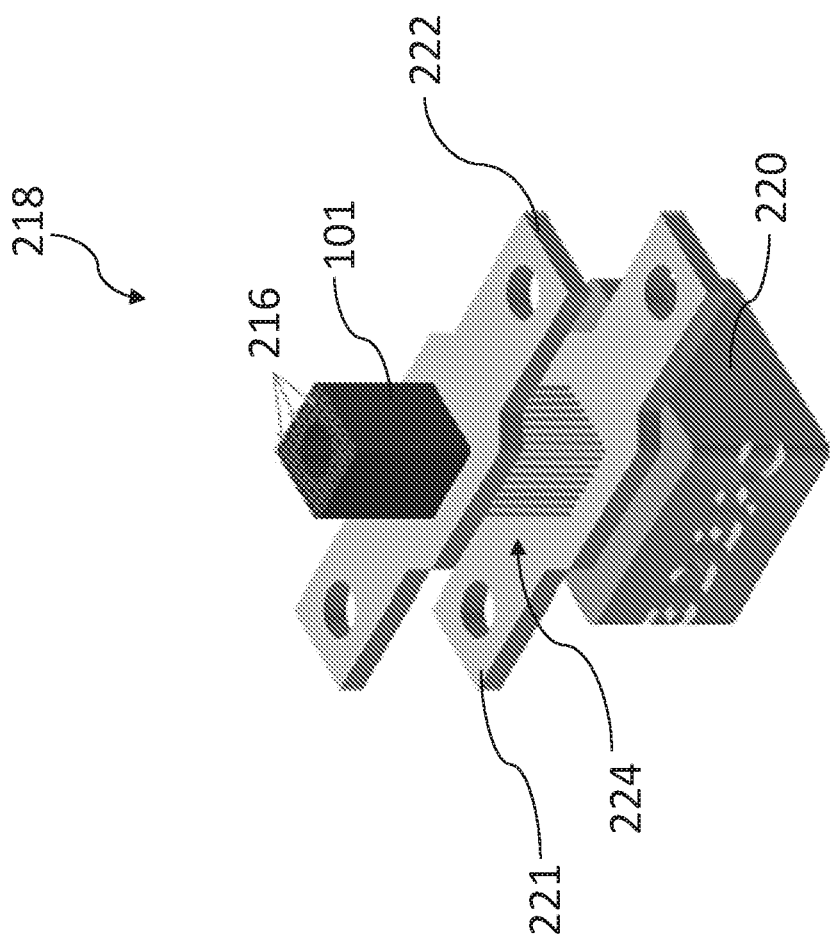
FIG. 21 shows a perspective view of a tissue construct and a platen of the printing sample holder of FIG. 18 being removed from a base of the printing sample holder of FIG. 18.

Referring now to FIGS. 7-9, in various embodiments, housing 100 of bioreactor 10 may further include a cover 130. Cover 130 is configured to couple with lower housing 102 such that perfusion chamber 105 is sealed from the atmosphere, and infiltration of pathogens into chamber 105 and tissue construct 101 is prevented. In various embodiments, cover 130' may include an observing/analyzing portion 132, such as a window. Observing/analyzing portion 132 may be opaque or transparent, and may be formed of silicon or any other similar opaque or transparent materials. Observing/analyzing portion 132 is generally configured to facilitate transmission of a signal from sensors, such as an ultrasound Doppler probe, a camera, an IR device, or other similar sensors, into perfusion chamber 105 such that tissue construct 101 can be observed, analyzed and/or manipulated within perfusion chamber 105. For example, the ultrasound Doppler probe can be used to analyze, and therefore, control fluid flow characteristics, such as flow velocity and turbulent flow, for example, through observing/analyzing portion 132 such that a user has the ability to control cell differentiation and subsequent tissue formation aseptically in real-time. In addition, a camera may be used to observe tissue construct 101 aseptically and in real-time during perfusion and/or incubation. Furthermore, in various embodiments, cover 130 may be a linear actuation module or other modular component configured to provide shear, compressive, tensile and/or cyclic stress or strain or other manipulation to tissue construct 101 to simulate natural tissue activity aseptically in real-time.

Referring now to FIGS. 10-17, sample holder 200 generally includes a base 202 and a platen 204, where base 202 includes a perfusion channel 206 and platen 204 includes at least one perfusion opening 207. In various embodiments, platen 204 may be formed of a biomaterial that facilitates direct cell adhesion, while in other various embodiments, sample holder 200 may further include a construct support 208. Platen 204 and/or construct support 208 are configured to support tissue construct 101 such that perfusion opening(s) 207 of platen 204 align with at least one of perfusion channel(s) 216 in tissue construct 101. In general, platen 204 is stacked on base 202 such that a bottom surface of platen 204 abuts a top surface of base 202, and perfusion channel 206 within base 202 aligns with perfusion opening(s) 207 of platen 204 and at least one of perfusion channel(s) 216 of tissue construct 101 to supply fluid through platen 204 and tissue construct 101. In various embodiments, construct support 208 includes an adhesive interface, such as collagen, tissue adhesive, gelatin, or other similar materials, applied to an upward-facing surface of platen 204. The adhesive interface allows cells of tissue construct 101 to adhere to platen 204. In embodiments, base 202 can be a module which holds platen 204 containing tissue construct 101. In various embodiments, sample holder 200 is inserted in a space defined by upper surface 129 of bottom 109 of lower housing 102 (FIG. 3) such that the module having base 202, platen 204 and tissue construct 101 is secured in the space.

With reference to FIGS. 10, 11, 14, and 15, in various embodiments, platen 204 is held in abutment with base 202 of sample holder 200 by securing extensions 210 extending upward from base 202. Securing extensions 210 are configured to further hold platen 204, and thus tissue construct 101, in place to allow fluid to perfuse through tissue construct 101 without displacing platen 204. When sample holder 200 includes securing extensions 210 on base 202, platen 204 may be removed from base 202 by sliding platen 204 horizontal out from under securing extensions 210 or snapping platen 204 from under securing extensions 210.

Referring to FIGS. 14-17, platen 204* may also, in various embodiments, have handling extensions 212. Handling extensions 212 extend upward from an upper surface of platen 204*, and allow a user to handle or remove platen 204*, and thus tissue construct 101, from sample holder 202* when desired. Furthermore, in various embodiments, platen 204* may further include a skirt 214 extending from a bottom surface of platen 204*. Skirt 214 allows platen 204* to better couple with base 202* such that a fluid tight seal may be formed between platen 204* and base 202*.

In operation, a single piece of tubing 121 is generally first coupled to inlet port 112 and outlet port 114 of bioreactor 10 to maintain sterility and avoid contamination of the medium/fluid and tissue construct 101. Subsequently, a fluid, such as nutrient enriched culture medium or other various fluids discussed above, is poured into perfusion chamber 105 and tubing 121 and tissue construct 101 is placed within bioreactor 10. In various embodiments, tissue construct 101 may be placed within bioreactor 10 before or after the fluid is poured into bioreactor 10. Tissue construct 101 may be placed within bioreactor 10 by either placing platen 204 with a bioprinted tissue construct 101 adhered thereto within perfusion chamber 105 of bioreactor 10 or printing tissue construct 101 directly into perfusion chamber 105 of bioreactor 10. Tissue construct 101 may be printed via any various bioprinting method, for example via scaffold-free or scaffold dependent methods (e.g., Kenzan method, centrifugation, molding method, magnetic bioprinting, inkjet printing, laser assisted bioprinting, freeform reversible embedding of suspended hydrogels (FRESH) bioprinting, layer-by-layer bioprinting, modular-assembly bioprinting, automated assembly, manual assembly, cell self-assembly, extrusion), or via any other bioprinting method.

With reference to FIGS. 18-21, tissue construct 101 may be printed onto a printing sample holder 218. In various embodiments, printing sample holder 218 may be positioned within bioreactor 10 which is placed within a bioprinter (not shown). In general, printing sample holder 218 includes a base 220, a first platen 221, and a second platen 222. In various embodiments, platen 222 may be the same as platen 204 such that platen 222 can be used with printing sample holder 218 and removed and coupled to base 202 of sample holder 200. Printing sample holder 218 may include a flat surface and/or various structures, such as needles, poles, or stumps 224, for example, which are capable of creating channels 216 within construct 101 once removed. Structures 224 are generally coupled to first platen 221 and extend through openings within second plate 222 such that when second platen 222 is removed from base 220 and first platen 221, tissue construct 101 is removed from structures 224 creating microchannels 216 within tissue construct 101 (see FIG. 21).

Once tissue construct 101 is placed within bioreactor 10, bioreactor 10 may be transported to a desired area, coupled to a pump 120 and/or tissue construct 101 may be analyzed, manipulated and/or observed. In various embodiments, lid 130 may be placed onto lower housing 102 sealing off perfusion chamber 105 before, during or after bioreactor 10 is transferred.

The desired area for bioreactor 10 to be transferred to may, in various embodiments, include a countertop where bioreactor 10 can be coupled to a pump 120 such that fluid/medium can be perfused through tissue construct 101. In other various embodiments, the desired area may be an incubator (not shown) where tissue construct 101 can be incubated without removing the bioprinted tissue construct 101 from perfusion chamber 105. In yet other various embodiments, bioreactor 10 may be placed in an incubator and coupled to pump 120 via tubing 121 such that tissue construct 101 can be perfused and incubated concurrently. In various other embodiments, bioreactor 10 may be transferred to a workspace where construct 101 can be further manipulated within chamber 105 prior to or following placement in the incubator. The workspace may include a cell and tissue culture hood, a biosafety cabinet, or other various sterile atmospheres. Being able to transport, perfuse, manipulate, and/or incubate the tissue construct 101 without removing it from bioreactor 10, allows a user to mitigate the risks associated with handling tissue construct 101 and transferring tissue construct 101 from the printing vessel to the culture/perfusion vessel.

In various embodiments, cameras with or without visible light, Doppler capable ultrasound probes, or other observing or analyzing devices and sensors may be either coupled to analyzing port 116 or operated through window 132 to image, analyze, or otherwise stimulate tissue construct 101. Observing the construct during printing and/or incubation post-printing, allows a user to properly stimulate or perfuse tissue construct 101 to better duplicate the stimulation and perfusion required by the specific tissue it is replacing. Observing the construct 101 also allows a user to track construct 101 behavior in real-time and over an extended period of time. In addition, the modular nature of bioreactor 10 allows different imaging devices or other sensors to be fitted to the bioreactor 10 while maintaining sterility.

Figure 23:
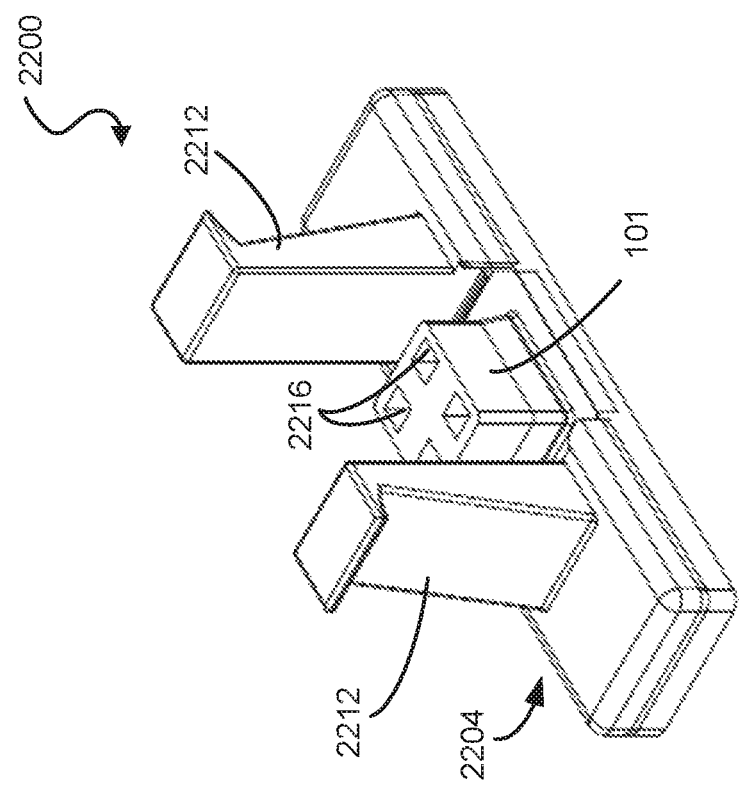
FIG. 23 shows a perspective view of the platen-sleeve subassembly of FIG. 22 without the sleeve.
Figure 22:
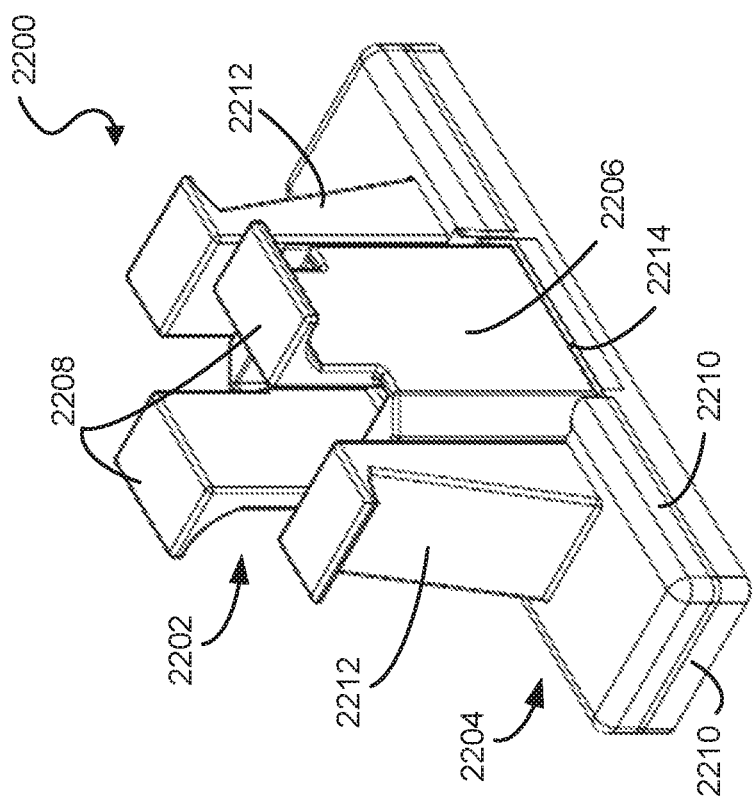
FIG. 22 shows a perspective view of a platen-sleeve subassembly of the present disclosure including a sleeve and a platen.

Referring now to FIGS. 22-23, in various embodiments, a platen-sleeve subassembly 2200 can be used as another sample holder. In FIG. 22, platen-sleeve subassembly 2200 includes a sleeve 2202 and a platen 2204. In embodiments, sleeve 2202 has a quadrilateral shape including four side walls 2206 and at least two of side walls 2206 has handling extensions 2208 extending upward from an upper surface of sleeve 2202 for allowing a user to handle or remove sleeve 2202 from platen-sleeve subassembly 2200. Similarly, platen 2204 has a quadrilateral shape including four sides 2210 and at least two handling extensions 2212 extending upward from an upper surface of platen 2204 for allowing the user to handle or remove platen-sleeve subassembly 2200 from housing 100 of bioreactor 10 (FIG. 1). Although the quadrilateral shape is shown for sleeve 2202 and platen 2204, other suitable geometric shapes, such as cylindrical or oval configurations, can be used to suit different applications.

In the illustrated embodiment, platen 2204 can be coated with an adhesive interface, such as collagen, tissue adhesive, gelatin, or other similar materials, applied to an upward-facing surface of platen 2204. The adhesive interface promotes cell adhesion of tissue construct 101 to platen 2204 within platen-sleeve subassembly 2200. Sleeve 2202 can be temporarily sealed spheroid-tight either by friction fit or with biocompatible adhesive to platen 2204, thereby making platen-sleeve subassembly 2200. However, nutrients can still pass through a junction 2214 between sleeve 2202 and platen 2204.

Figure 24:
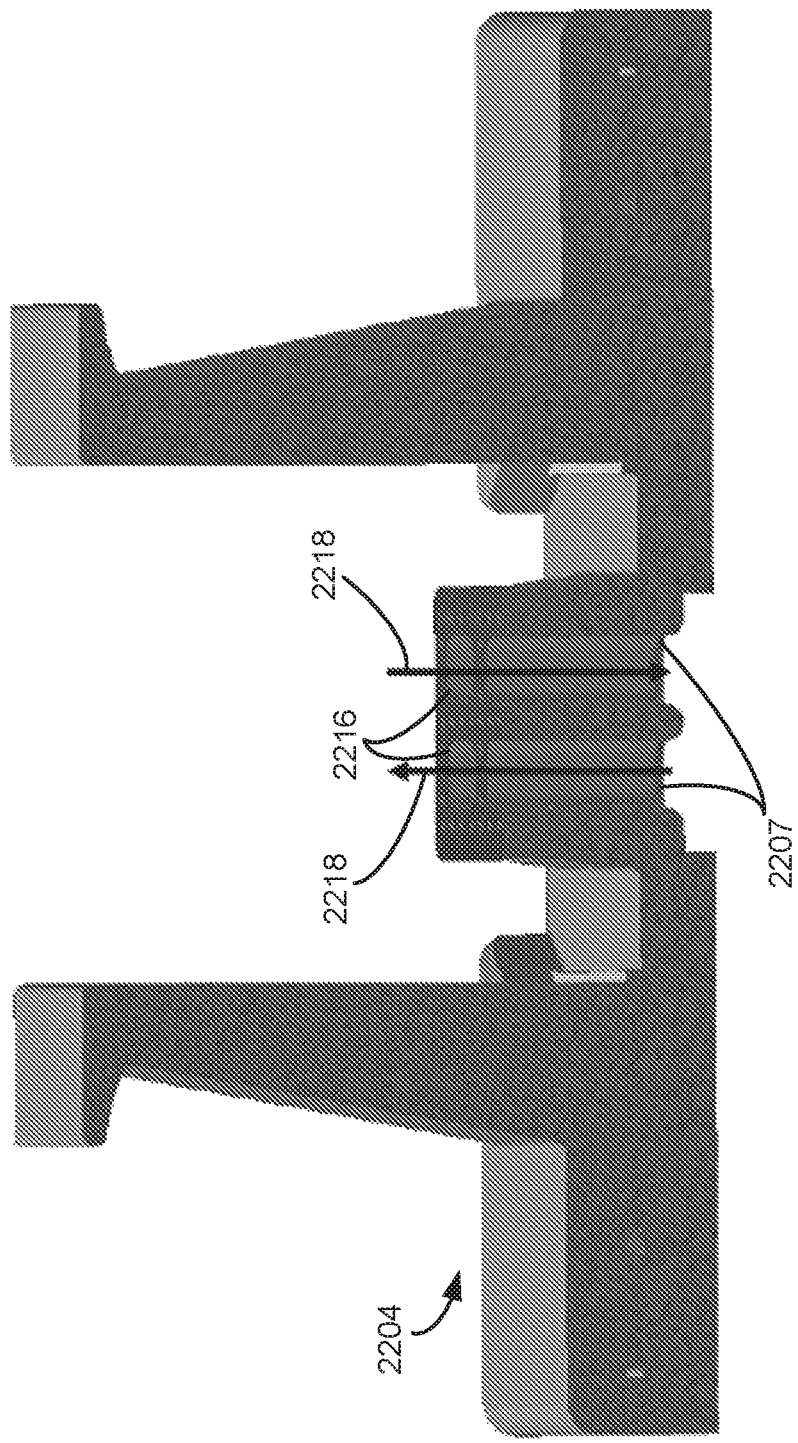
FIG. 24 shows a cross-sectional view of the platen-sleeve subassembly of FIG. 23.

Referring now to FIGS. 23-24, in various embodiments, sleeve 2202 and/or platen 2204 are configured to support tissue construct 101 such that perfusion opening(s) 2207 of platen 2204 align with at least one of perfusion channel(s) 2216 in tissue construct 101. Thus, the nutrients can pass through perfusion openings(s) 2207 and perfusion channel(s) 2216 as illustrated in arrows 2218.

Figure 26:
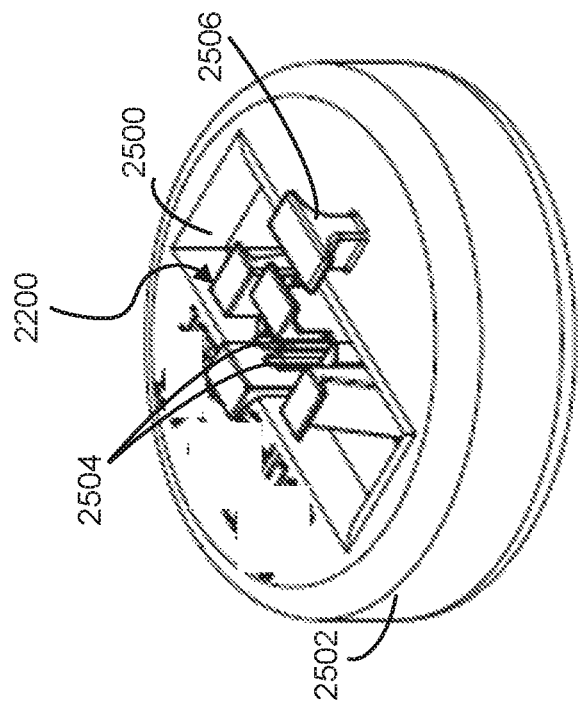
FIG. 26 shows a perspective view of the cast mold of FIG. 25 having the platen-sleeve subassembly of FIG. 22.
Figure 25:
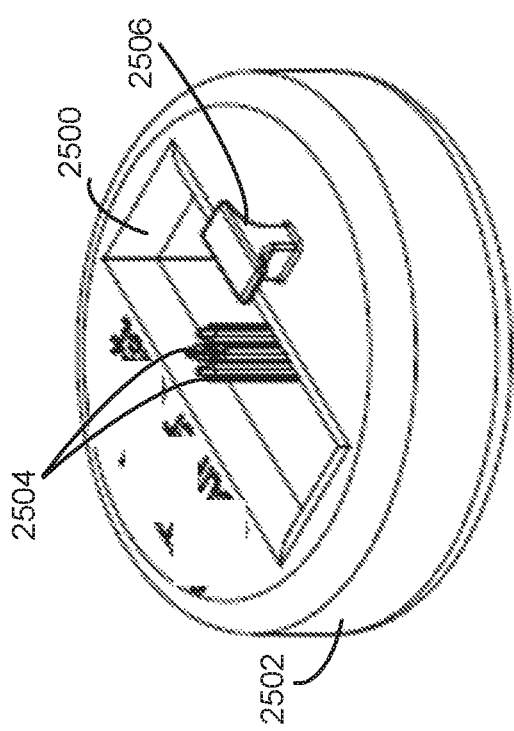
FIG. 25 shows a perspective view of a cast mold used with the platen-sleeve subassembly of FIG. 22.

Referring now to FIGS. 25-26, in various embodiments, platen-sleeve subassembly 2200 can be placed into a cavity 2500 formed on a top surface of a cast mold 2502 having a substantially cylindrical body. Cavity 2500 includes one or more tines or needles (e.g., poles or stumps) 2504 extending upward from an inner bottom surface of cavity 2500 such that each needle 2504 corresponds with at least one perfusion opening 2207 of platen 2204 and at least one perfusion channel 2216 of tissue construct 101.

For example, platen-sleeve subassembly 2200 can be inserted into cavity 2500 of cast mold 2502 over needles 2504 of cast mold 2502 such that needles 2504 penetrate corresponding perfusion opening(s) 2207 of platen 2204 and perfusion channel(s) 2216 of tissue construct 101. Then, cellular spheroids or other biological material and medium are poured into cavity 2500 of cast mold 2502. In embodiments, the medium can also be in the space within cast mold 2502 surrounding platen-sleeve subassembly 2200. As such, the biological material is allowed to mature. For example, in a spheroid case, the spheroids are allowed to fuse into tissue construct 101 providing simultaneous molding and platen adhesion. In embodiments, cast mold 2502 includes one or more handling extensions 2506 extending upward from an upper surface of cast mold 2502 for easy handling.

Figure 27:
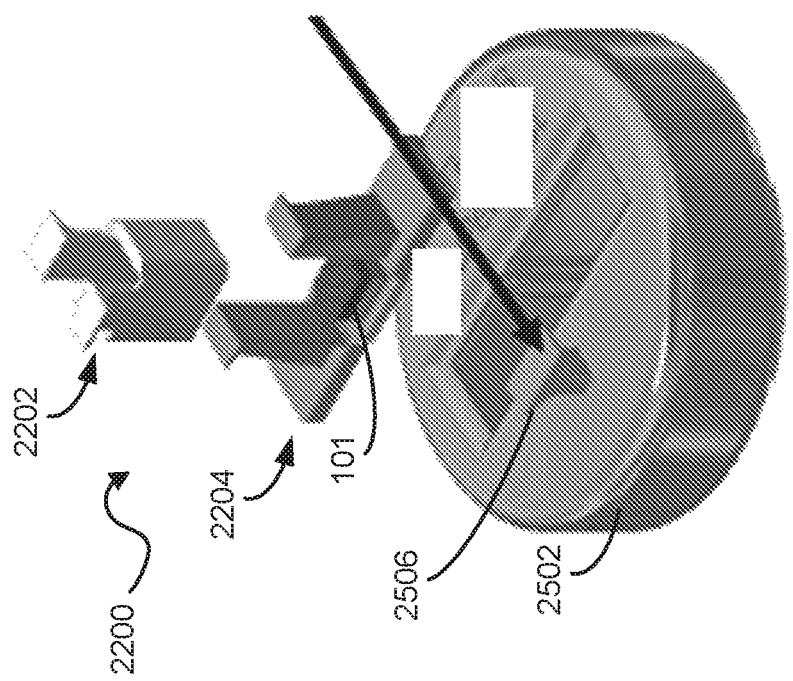
FIG. 27 shows an exploded view of the cast mold of FIG. 26.

Referring now to FIG. 27, after a predetermined fusion period, platen-sleeve subassembly 2200 having tissue construct 101 can be removed from cast mold 2502. Tissue construct 101 is held to platen 2204 through adhesion or other means (e.g., sleeve 2202). When tissue construct 101 is removed, a mold design including perfusion channel(s) 2216 of tissue construct 101 is created (e.g., microchannels). Notably, tissue construct 101 has a self-supporting feature where tissue construct 101 having the microchannels can withstand its own weight without or independent of any supporting structures. For example, the self-supporting features are created by cells in tissue construct 101 and an extracellular matrix the cells secrete during the fusion period. Sleeve 2202 is designed to contain the spheroids during fusion but sleeve 2202 can be treated to prevent cell adhesion so the resulting tissue is not supported by sleeve 2202 but by its own cells and the extracellular matrix. Further, in a bioink case, the resulting tissue can also be self-supporting when the tissues are perfused with platen-aligned microchannels and the self-supporting feature without any separate support structure. Depending on a shape of sleeve 2202, tissue construct 101 can be any geometric shape, such as cylindrical or square column shapes. Although one platen 2204 is shown for illustration purposes, any number of platens can be used to suit different applications. Suitable arrangements of platens 2204 are contemplated, e.g., a top-bottom configuration and a side-to-side configuration.

Figure 28:
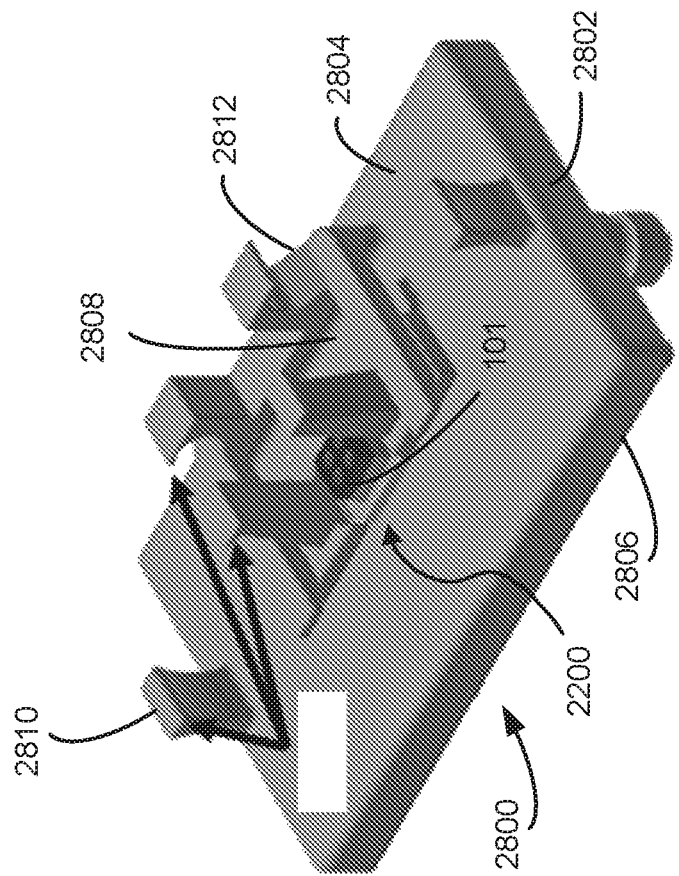
FIG. 28 shows a perfusion module of the present disclosure having the platen-sleeve subassembly of FIG. 22.

Referring now to FIG. 28, a perfusion module 2800 can be used with platen-sleeve subassembly 2200 and has a quadrilateral column body. For example, perfusion module 2800 can be inserted into perfusion chamber 105 of bioreactor 10. Platen-sleeve subassembly 2200 having tissues is placed onto perfusion module 2800. Perfusion module 2800 has a rectangular shape when viewed from above and includes four sides 2802, a top side 2804, and a bottom side 2806. In FIG. 28, platen-sleeve subassembly 2200 can be placed into an indent 2808 formed on top side 2804 of perfusion module 2800. The tissues can be perfused with sleeve 2202 in place (without removing sleeve 2202), if desired. In some embodiments, however, sleeve 2202 is removed to leave tissue construct 101 for tissue perfusion such that the fluid can travel through tissue construct 101, platen 2204, and perfusion channel(s) 2216 of tissue construct 101 unimpeded in a predetermined flow path, thereby allowing the tissue perfusion. As with cast mold 2502, perfusion module 2800 also includes one or more handling extensions 2810 extending upward from top side 2804 of perfusion module 2800 for easy handling. A holder 2812 can be used to securely hold platen-sleeve subassembly 2200 having tissue construct 101 in indent 2808 of perfusion module 2800.

Figure 29:
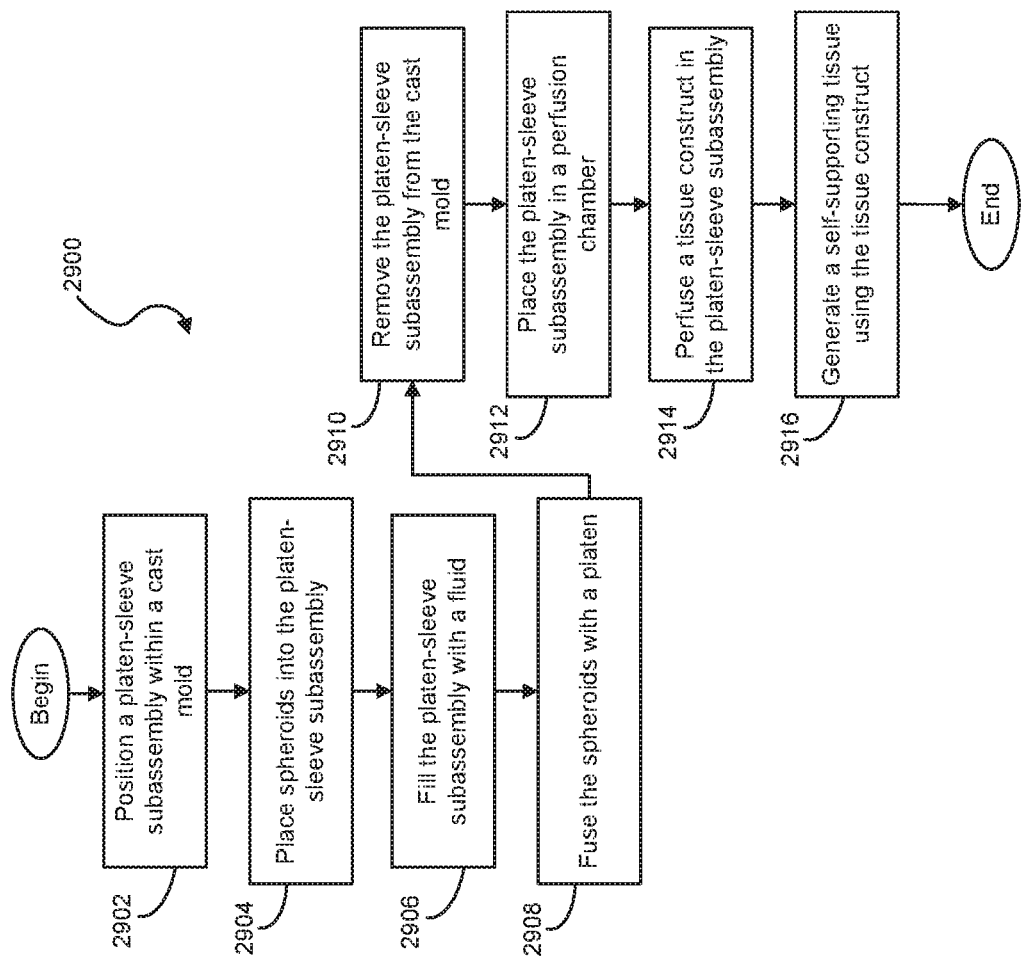
FIG. 29 shows a flow chart of a method for biofabricating a scaffold-free tissue in accordance with embodiments of the present disclosure.

Referring now to FIG. 29, an illustrative method 2900 for biofabricating a scaffold-free tissue is shown. It will be described with reference to FIGS. 1-28. However, any suitable structure can be employed. Although sub-blocks 2902-2916 are illustrated, other suitable sub-blocks can be employed to suit different applications. It should be understood that the blocks within the method can be modified and executed in a different order or sequence without altering the principles of the present disclosure.

At block 2902, a user or a robotic system (not shown) positions platen-sleeve subassembly 2200 within cavity 2500 of cast mold 2502 such that needles 2504 of cast mold 2502 are inserted into corresponding perfusion opening(s) 2207 of platen 2204.

At block 2904, cellular spheroids can be placed into platen-sleeve subassembly 2200 such that the spheroids contact with a floor or surface of platen 2204 to be adhered to or otherwise secured to the floor. Platen-sleeve subassembly 2200 can be temporarily or removably coupled to cast mold 2502.

At block 2906, platen-sleeve subassembly 2200 can be filled with a fluid. For example, the fluid can provide a passage of nutrients and media using an interface, such as junction 2214, between platen 2204 and walls of the platen (e.g., sleeve 2202).

At block 2908, the spheroids are fused with platen 2204 after a predetermined fusion period.

At block 2910, platen-sleeve assembly 2200 is removed from cast mold 2502 after the predetermined fusion period and placed onto perfusion module 2800.

At block 2912, perfusion module 2800 is placed in perfusion chamber 105 of bioreactor 10, e.g., using the robotic system.

At block 2914, a negative volume is created when cast mold 2502 is removed to generate channels in the resulting biofabricated tissue (e.g., tissue construct 101). The channels are intrinsically aligned with perfusion opening(s) 2207 in platen 2204 such that the fluid can be perfused through platen 2204 and tissue construct 101.

At block 2916, a self-supporting tissue is generated, using tissue construct 101, which is adhered to platen 2204 having perfusion opening(s) 2207 aligned with perfusion channel(s) 2216 in tissue construct 101 without using intervening non-tissue materials penetrating through tissue construct 101. Any of the blocks 2902-2916 can be repeated as desired.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A bioreactor for flowing a liquid medium through one or more through channels in a tissue construct, the bioreactor comprising:
   a housing that defines a single interior chamber in the bioreactor, the interior chamber having a floor, side walls and a cover, where the interior chamber receives the liquid medium and the tissue construct to be cultured;
   a tissue construct holder in the interior chamber, the tissue construct holder comprising:
   a base on the interior chamber floor, the base having a bottom surface, a top surface, and an opening extending completely through the base, and,
   a first platen having a bottom surface, a top surface, and an opening extending completely through the first platen, where the first platen is removably secured to the base and the bottom surface of the first platen abuts the top surface of the base and where the opening in the base and the opening in the first platen align and are also alignable with the one or more through channels of the tissue construct;

a second platen having a bottom surface, a top surface, and an opening extending completely through the second platen, where the top surface of the second platen is configured to securely hold the channeled tissue construct, where the second platen is removably secured to the first platen and the bottom surface of the second platen abuts the top surface of the first platen and where the opening in the base, the opening in the first platen, and the opening in the second platen align and are also all alignable with the one or more through channels of the tissue construct;

wherein the openings align along a common vertical axis;

wherein the top surface of the first platen and the bottom surface of the second platen are planar;

a first port coupled to an outside of the housing;

a second port coupled to the outside of the housing;a first liquid medium flow channel in the housing that extends from the first port through the chamber floor and communicates with the opening in the bottom surface of the base of the tissue construct holder such that a first liquid medium flow path exists between the first liquid medium flow channel, the opening in the base, the opening in the first platen, an opening in the second platen, and the one or more through channels of the tissue construct; and, a second liquid medium flow channel in the housing that extends from the second port through the chamber housing to an opening in the interior chamber such that a second liquid medium flow path exists between the second liquid medium flow channel and the interior chamber opening.

2. The bioreactor of claim 1, where the first port coupled to the outside of the housing is an inlet port and the second port coupled to the outside of the housing is an outlet port.

3. The bioreactor of claim 1, where the first port coupled to the outside of the housing is an outlet port and the second port coupled to the outside of the housing is an inlet port.

4. The bioreactor of claim 1, further comprising a third port coupled to the outside of the housing.

5. The bioreactor of claim 1, where the bioreactor comprises a 3D printed material.

6. The bioreactor of claim 1, where the base of the tissue construct holder includes two separate extensions extending upwards from the top surface of the base to receive and to securely hold the first platen.

7. The bioreactor of claim 1, further comprising an observing/analyzing port.

8. The bioreactor of claim 1, where the cover is coupled with the housing and seals the chamber.

9. The bioreactor of claim 1, where the cover comprises an observing/analyzing portion.

10. The bioreactor of claim 1, where the first platen includes at least one extension extending upwards from the top surface of the first platen.

11. The bioreactor of claim 1, where the first platen further comprises at least one channel-creating element projecting upward from the top surface of the first platen.

12. The bioreactor of claim 1, where the first platen further comprises at least one channel-creating element projecting upward from the top surface of the first platen and where the at least one channel-creating element of the first platen is selected from the group consisting of a tine, a needle, a pole and a stump.

13. The bioreactor of claim 1, where the top surface of the first platen is configured to securely hold the channeled tissue construct and where the top surface of the first platen comprises an adhesive coating.

14. The bioreactor of claim 1, where the top surface of the first platen is configured to securely hold the channeled tissue construct and where the top surface of the first platen is free of an adhesive coating.

15. The bioreactor of claim 1, where the first platen further comprises a sleeve.

16. The bioreactor of claim 1, where the first platen further comprises a sleeve and the sleeve is temporarily sealable to the platen.

17. The bioreactor of claim 1, where the first platen further comprises a sleeve and where the sleeve further comprises at least one extension extending upward from a top surface of the sleeve.

18. The bioreactor of claim 1, where the first platen further comprises a sleeve and where a junction is disposed between the sleeve and the first platen.

19. The bioreactor of claim 1, where the sleeve comprises a treatment to prevent cell adhesion.

20. A bioreactor for flowing a liquid medium through and inside at least one channel in a tissue construct, the bioreactor consisting of:

a housing that defines a single interior chamber in the bioreactor, the interior chamber having a floor, side walls and a cover, where the interior chamber receives the liquid medium and the channeled tissue construct to be cultured;

a tissue construct holder in the interior chamber, the tissue construct holder having:

a base on the interior chamber floor, the base having a bottom surface, a top surface, and an opening extending completely through the base, and, a first platen having a bottom surface, a top surface, and an opening extending completely through the first platen, where the first platen is removably secured to the base and the bottom surface of the first platen abuts the top surface of the base and where the opening in the base and the opening in the first platen align and are also alignable with the through channel of the tissue construct;

a first port coupled to an outside of the housing;

a second port coupled to the outside of the housing;

a first liquid medium flow channel in the housing that extends from the first port though the chamber floor and communicates with the opening in the bottom surface of the base of the tissue construct holder such that a first liquid medium flow path exists between the first liquid medium flow channel, the opening in the base, the opening in the platen and the through channels of the tissue construct; and, a second liquid medium flow channel in the housing that extends from the second port through the chamber housing to an opening in the interior chamber such that a second liquid medium flow path exists between the second liquid medium flow channel and the interior chamber opening.

21. A bioreactor for flowing a liquid medium through one or more through channels in a tissue construct, the bioreactor comprising:

a housing that defines a single interior chamber that receives the liquid medium and the tissue construct to be cultured in the bioreactor;

a tissue construct holder in the interior chamber comprising:

a base having a top surface and an opening extending completely through the base, a first platen having a bottom surface, a top surface, and an opening extending completely through the first platen, where the first platen is removably secured to the base and the bottom surface of the first platen abuts the top surface of the base and where the opening in the base and the opening in the first platen align and are also alignable with the one or more through channels of the tissue construct; and a second platen having a bottom surface, a top surface, and an opening extending completely through the second platen, where the top surface of the second platen is configured to securely hold the channeled tissue construct, where the second platen is removably secured to the first platen and the bottom surface of the second platen abuts the top surface of the first platen and where the opening in the base, the opening in the first platen, and the opening in the second platen align and are also all alignable with the one or more through channels of the tissue construct;

wherein the top surface of the first platen and the bottom surface of the second platen are planar, and wherein the openings align along a common vertical axis.

* * * * *